US012268805B2

(12) United States Patent
Randolph et al.

(10) Patent No.: US 12,268,805 B2
(45) Date of Patent: Apr. 8, 2025

(54) DRESSING WITH INTEGRATED PUMP AND RELEASABLY COUPLED PUMP ACTUATOR

(71) Applicant: KCI Licensing, Inc., San Antonio, TX (US)

(72) Inventors: Larry Tab Randolph, San Antonio, TX (US); Sara Cinnamon, San Francisco, CA (US); Stefan Foulstone, San Francisco, CA (US); Charles Hartzell, San Mateo, CA (US); Stephanie Henze, San Mateo, CA (US); Robert Lane, Larkspur, CA (US); Colton Sanford, San Francisco, CA (US)

(73) Assignee: KCI Licensing, Inc., San Antonio, TX (US)

( * ) Notice: Subject to any disclaimer, the term of this patent is extended or adjusted under 35 U.S.C. 154(b) by 16 days.

(21) Appl. No.: 17/599,229

(22) PCT Filed: Mar. 26, 2020

(86) PCT No.: PCT/US2020/025035
§ 371 (c)(1),
(2) Date: Sep. 28, 2021

(87) PCT Pub. No.: WO2020/205448
PCT Pub. Date: Oct. 8, 2020

(65) Prior Publication Data
US 2022/0176032 A1 Jun. 9, 2022

Related U.S. Application Data

(60) Provisional application No. 62/826,382, filed on Mar. 29, 2019.

(51) Int. Cl.
*A61M 1/00* (2006.01)
*A61F 13/05* (2024.01)
*A61M 39/06* (2006.01)

(52) U.S. Cl.
CPC ............... *A61M 1/82* (2021.05); *A61F 13/05* (2024.01); *A61M 1/684* (2021.05); *A61M 1/915* (2021.05);
(Continued)

(58) Field of Classification Search
CPC .... Y10T 74/18088; F04B 43/04; F04B 35/01; F04B 35/04; F04B 2203/02; F04B 45/02;
(Continued)

(56) References Cited

U.S. PATENT DOCUMENTS

| 1,355,846 A | 10/1920 | Rannells |
| 1,454,207 A | 5/1923 | Bemis |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for Corresponding Application No. PCT/US2019/044227, dated Dec. 18, 2019.
(Continued)

*Primary Examiner* — Guy K Townsend
*Assistant Examiner* — Seth Han

(57) ABSTRACT

A dressing for treating a tissue site with negative pressure including a tissue interface, a cover, a chamber wall, and a base. The cover may be adapted to be sealed to epidermis proximate the tissue site. The chamber wall may define a pump chamber, wherein the pump chamber may be adapted to be fluidly coupled to the tissue interface. The base may extend from the chamber wall, wherein the base may be fluidly sealed to the cover. The dressing may include an intake valve and an exhaust valve fluidly coupled to the pump chamber. The pump chamber may be compressed to
(Continued)

evacuate fluid from the pump chamber through the exhaust valve. The pump chamber may then be expanded to draw' fluid through the intake valve from the tissue interface. This supplies a negative pressure to the tissue interface which may be adapted to distribute negative pressure across the tissue site.

14 Claims, 32 Drawing Sheets

(52) U.S. Cl.
CPC ............ *A61M 1/962* (2021.05); *A61M 39/06* (2013.01); *A61M 2039/0646* (2013.01)

(58) Field of Classification Search
CPC .. F04B 45/027; F04B 9/127; F04B 2201/021; A61M 1/962; A61M 1/80; A61M 1/68; A61M 1/82; A61M 1/684
See application file for complete search history.

(56) References Cited

U.S. PATENT DOCUMENTS

| | | |
|---|---|---|
| 1,557,978 A | 10/1925 | Cameron |
| 1,631,274 A | 6/1927 | Hubert |
| 1,671,992 A | 6/1928 | Mannborg |
| 1,726,584 A | 9/1929 | Persons |
| 1,767,320 A | 6/1930 | Oreste |
| 2,060,063 A | 11/1936 | Frimand |
| 2,324,173 A | 7/1943 | Porter |
| 2,547,758 A | 4/1951 | Keeling |
| 2,553,247 A | 5/1951 | Fowler |
| 2,609,000 A | 9/1952 | Mowbray |
| 2,632,443 A | 3/1953 | Lesher |
| 2,682,873 A | 7/1954 | Evans et al. |
| 2,816,703 A | 12/1957 | Turner |
| 2,910,763 A | 11/1959 | Lauterbach |
| 2,969,057 A | 1/1961 | Simmons |
| 3,066,672 A | 12/1962 | Crosby, Jr. et al. |
| 3,263,679 A | 8/1966 | Hass |
| 3,367,332 A | 2/1968 | Groves |
| 3,487,832 A | 1/1970 | Spence |
| 3,520,300 A | 7/1970 | Flower, Jr. |
| 3,568,675 A | 3/1971 | Harvey |
| 3,648,692 A | 3/1972 | Wheeler |
| 3,663,122 A | 5/1972 | Kitchen |
| 3,682,180 A | 8/1972 | McFarlane |
| 3,802,424 A | 4/1974 | Newell |
| 3,826,254 A | 7/1974 | Mellor |
| 3,861,217 A | 1/1975 | Rabenecker et al. |
| 3,938,514 A * | 2/1976 | Boucher ............ A61M 3/0262 222/206 |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,453,538 A | 6/1984 | Whitney |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,870,962 A | 10/1989 | Sitnik |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,113,599 A | 5/1992 | Cohen et al. |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,439,104 B1 | 8/2002 | Tonogai et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 6,916,301 B1 | 7/2005 | Clare |
| 7,290,660 B2 | 11/2007 | Tilman et al. |
| 7,762,973 B2 | 7/2010 | Einarsson et al. |
| 7,837,387 B2 | 11/2010 | Newrones et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |

(56) References Cited

U.S. PATENT DOCUMENTS

| | | | |
|---|---|---|---|
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,119,705 | B2 | 9/2015 | Parish et al. |
| 9,198,801 | B2 | 12/2015 | Weston |
| 9,211,365 | B2 | 12/2015 | Weston |
| 9,289,542 | B2 | 3/2016 | Blott et al. |
| 9,510,965 | B2 | 12/2016 | Grim et al. |
| 10,383,773 | B2 | 8/2019 | Han |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2002/0173774 | A1 | 11/2002 | Olsen |
| 2004/0030304 | A1 | 2/2004 | Hunt et al. |
| 2004/0215120 | A1 | 10/2004 | Jensen et al. |
| 2005/0203452 | A1 | 9/2005 | Weston et al. |
| 2006/0025727 | A1* | 2/2006 | Boehringer ........... A61M 1/966 604/313 |
| 2006/0071965 | A1 | 4/2006 | Igarashi et al. |
| 2007/0092167 | A1 | 4/2007 | Tilman et al. |
| 2007/0167884 | A1 | 7/2007 | Mangrum et al. |
| 2008/0199335 | A1 | 8/2008 | Melatti |
| 2008/0249443 | A1 | 10/2008 | Avitable et al. |
| 2008/0319362 | A1 | 12/2008 | Joseph |
| 2009/0069731 | A1 | 3/2009 | Parish et al. |
| 2009/0124944 | A1 | 5/2009 | Ravikumar |
| 2009/0125004 | A1* | 5/2009 | Shen ................. A61M 1/80 417/413.1 |
| 2009/0234259 | A1 | 9/2009 | Hardman et al. |
| 2009/0234260 | A1 | 9/2009 | Coward et al. |
| 2010/0179463 | A1 | 7/2010 | Greener et al. |
| 2010/0210986 | A1 | 8/2010 | Sanders et al. |
| 2010/0268198 | A1 | 10/2010 | Buan et al. |
| 2011/0004168 | A1* | 1/2011 | Eriksson ........... A61F 13/00068 604/290 |
| 2011/0077570 | A1 | 3/2011 | Findeisen |
| 2011/0112492 | A1 | 5/2011 | Bharti et al. |
| 2011/0282309 | A1 | 11/2011 | Adie et al. |
| 2012/0041399 | A1 | 2/2012 | Blott et al. |
| 2012/0116299 | A1* | 5/2012 | Tack .................. A61M 1/06 604/74 |
| 2013/0090586 | A1 | 4/2013 | Dennis |
| 2013/0123722 | A1 | 5/2013 | Pratt et al. |
| 2013/0317406 | A1 | 11/2013 | Locke et al. |
| 2014/0163491 | A1 | 6/2014 | Schuessler et al. |
| 2014/0171837 | A1 | 6/2014 | Harcourt |
| 2014/0276288 | A1 | 9/2014 | Randolph et al. |
| 2015/0011980 | A1 | 1/2015 | Tan et al. |
| 2015/0057625 | A1 | 2/2015 | Coulthard |
| 2015/0080788 | A1 | 3/2015 | Blott et al. |
| 2015/0320603 | A1 | 11/2015 | Locke et al. |
| 2016/0213823 | A1 | 7/2016 | Walborn et al. |
| 2017/0100525 | A1 | 4/2017 | Heaton et al. |
| 2017/0239697 | A1 | 8/2017 | Oakner et al. |
| 2018/0228653 | A1 | 8/2018 | Kilpadi |
| 2018/0272052 | A1 | 9/2018 | Locke et al. |
| 2018/0328353 | A1 | 11/2018 | Timm |
| 2018/0353342 | A1 | 12/2018 | Locke et al. |
| 2019/0298580 | A1 | 10/2019 | Hall et al. |
| 2020/0038283 | A1 | 2/2020 | Hall et al. |
| 2020/0069476 | A1 | 3/2020 | Randolph et al. |
| 2020/0217312 | A1 | 7/2020 | Chang |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2010011148 A1 | 1/2010 |
| WO | 2011008497 A2 | 1/2011 |
| WO | 2013136181 A2 | 9/2013 |
| WO | WO-2016182977 A1 * | 11/2016 ....... A61F 13/00068 |
| WO | 2018213534 A1 | 11/2018 |
| WO | 2018217619 A1 | 11/2018 |
| WO | 2019002086 A2 | 1/2019 |

OTHER PUBLICATIONS

International Search Report and Written Opinion for corresponding application No. PCT/US2020/025019 dated Aug. 11, 2020.

International Search Report and Written Opinion for Corresponding Application No. PCT/US2020/025039, dated Jul. 9, 2020.

International Search Report and Written Opinion for corresponding Application No. PCT/US2020/025026, dated Aug. 24, 2020.

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

(56) References Cited

OTHER PUBLICATIONS

PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion for Corresponding Application No. PCT/US2020/025035 dated Jun. 18, 2020.
U.S. Non-Final Office Action for Corresponding U.S. Appl. No. 16/526,792, dated Oct. 27, 2022.
Chinese First Office Action Corresponding to Application No. 2020800255837, dated Apr. 25, 2022.
"Flexis Valve Labels from CCL" (https://ccllabel.com/portfolios/specialty-products-valves-labels/) 2019 CCL Industries.
Chinese Office Action for related application 2019800469852, dated Dec. 26, 2022.
Office Action for related U.S. Appl. No. 17/748,934, dated Apr. 5, 2023.
Office Action for related U.S. Appl. No. 17/748,934, dated Nov. 6, 2023.
Office Action for related U.S. Appl. No. 17/599,097, dated Nov. 8, 2023.
Office Action for related U.S. Appl. No. 16/526,792, dated Aug. 3, 2023.
Office Action for related U.S. Appl. No. 17/748,934, dated Feb. 9, 2024.
Japanese Office Action for related application 2021-504262, dated Mar. 26, 2024.
Office Action for related U.S. Appl. No. 17/748,934, dated Aug. 28, 2024.
Office Action for related U.S. Appl. No. 17/599,097, dated Sep. 6, 2024.

* cited by examiner

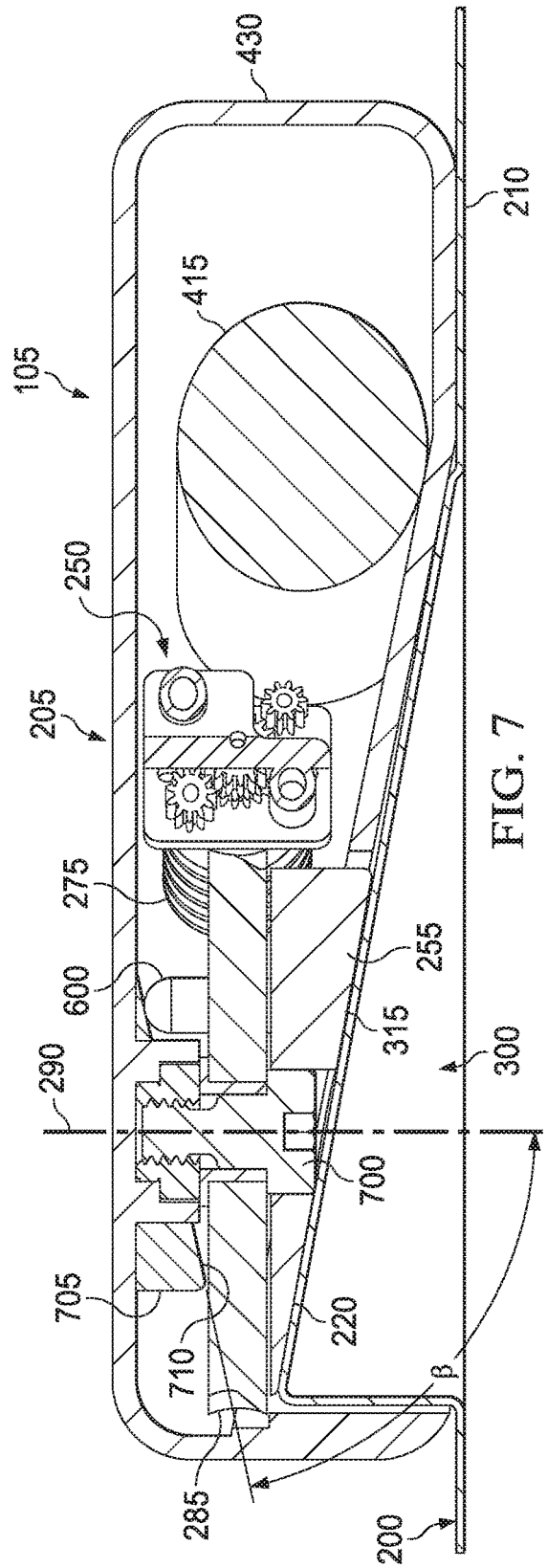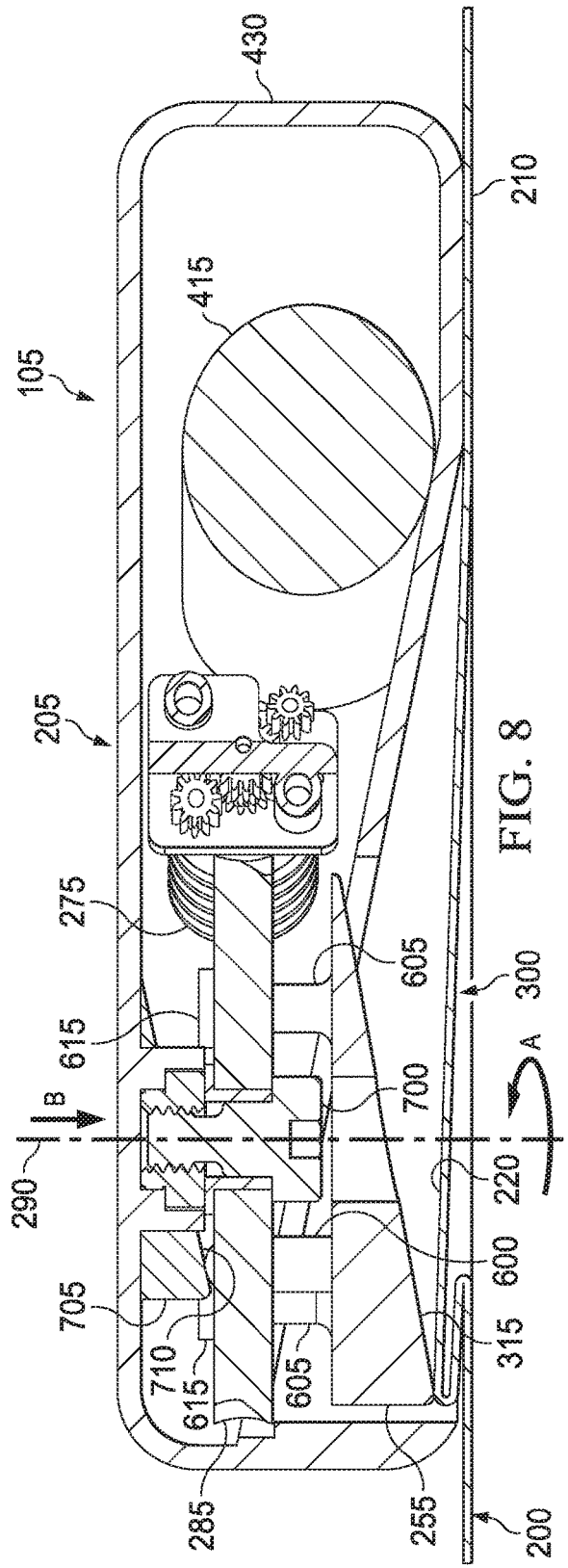

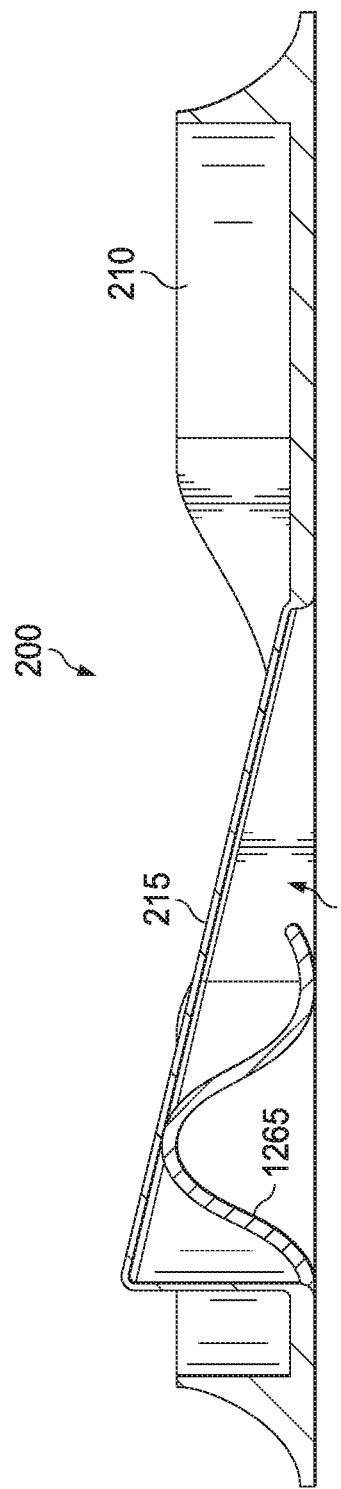
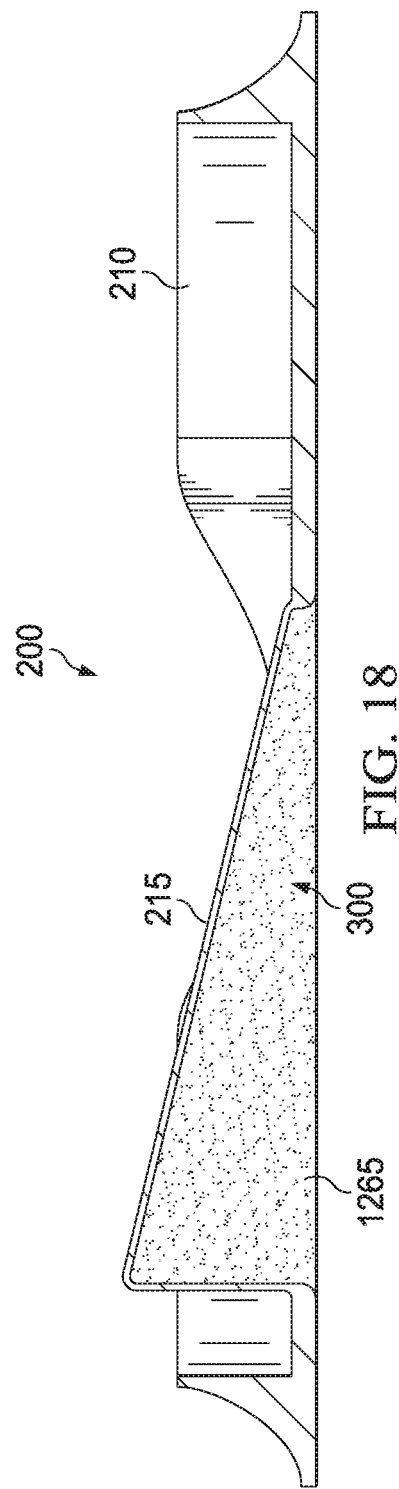

DRESSING WITH INTEGRATED PUMP AND RELEASABLY COUPLED PUMP ACTUATOR

RELATED APPLICATION

The present application claims priority to U.S. Provisional Patent Application No. 62/826,382, entitled "DRESSING WITH INTEGRATED PUMP AND RELEASABLY COUPLED PUMP ACTUATOR," filed Mar. 29, 2019, which is incorporated herein by reference for all purposes.

TECHNICAL FIELD

The invention set forth in the appended claims relates generally to tissue treatment systems and more particularly, but without limitation, to a negative-pressure source for applying negative pressure to dressings and methods of using the negative-pressure source for negative-pressure treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for a dressing including a negative-pressure source for use in a negative-pressure therapy environment are set forth in the appended claims. Illustrative embodiments are also provided to enable a person skilled in the art to make and use the claimed subject matter.

For example, in some embodiments, a dressing for treating a tissue site with negative pressure may include a tissue interface, a cover, a chamber wall, and a base. The cover may be adapted to be sealed to epidermis proximate the tissue site. The chamber wall may define a pump chamber, wherein the pump chamber may be adapted to be fluidly coupled to the tissue interface. The base may extend from the chamber wall, wherein the base may be fluidly sealed to the cover. The dressing may include an intake valve and an exhaust valve fluidly coupled to the pump chamber. The pump chamber may be compressed to evacuate fluid from the pump chamber through the exhaust valve. The pump chamber may then be expanded to draw fluid through the intake valve from the tissue interface. This supplies a negative pressure to the tissue interface which may be adapted to distribute negative pressure across the tissue site.

More generally, the tissue interface may be adapted to distribute negative pressure across the tissue site. The cover may be adapted to be sealed to epidermis proximate the tissue site. The chamber wall may define a pump chamber, wherein the pump chamber may be adapted to be fluidly coupled to the tissue interface. The base may extend from the chamber wall, wherein the base may be fluidly sealed to the cover.

In some embodiments, the dressing may further include an exhaust valve fluidly coupled to the pump chamber and adapted to allow fluid to be evacuated from the pump chamber if the chamber wall is compressed.

In some embodiments, the dressing may further include an intake valve between the tissue interface and the pump chamber, the intake valve adapted to fluidly couple the pump chamber and the tissue interface and adapted to allow pressure to be reduced in the tissue interface when the pump chamber is expanded.

A system for treating a tissue site with negative pressure is also described herein, wherein some example embodiments include a dressing and a pump actuator releasably coupled to the dressing. The dressing may comprise a tissue interface, a cover, and a pump. The tissue interface may be adapted to distribute negative pressure across the tissue site. The cover may be adapted to be sealed to epidermis proximate the tissue site. The pump may include a chamber wall and a base extending from the chamber wall. The chamber wall may define a pump chamber, wherein the pump chamber may be adapted to be fluidly coupled to the tissue interface. The base may be coupled to the cover to fluidly seal the pump chamber to the cover. The system may further include a pump actuator releasably coupled to the pump.

In some embodiments, the pump actuator may include a motor and a mechanism for compressing the pump chamber.

In some embodiments, pump actuator may include a motor and a mechanism for expanding the pump chamber.

In some embodiments, the pump actuator may include a motor and a mechanism for compressing and expanding the pump chamber.

A method for treating a tissue site with negative pressure is also described herein and may include the steps of applying a dressing to the tissue site and supplying negative pressure to the tissue site. The dressing may include a tissue interface adapted to distribute negative pressure across the tissue site, a cover adapted to be sealed to epidermis proximate the tissue site, and a pump. The pump may include a chamber wall, a base, an exhaust valve, and an intake valve. The chamber wall may define a pump chamber, wherein the pump chamber may be adapted to be fluidly coupled to the tissue interface. The base may extend from the chamber wall and may be fluidly sealed to the cover. The exhaust valve may be fluidly coupled with the pump chamber, and the intake valve may be fluidly coupled with the pump chamber and the tissue interface. The step of supplying negative pressure to the tissue site may include the steps of compressing the pump chamber to evacuate fluid from the pump chamber, and expanding the pump chamber to draw fluid from the tissue interface, through the intake valve, and into the pump chamber.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 7 is a section view of the negative-pressure source shown in FIG. 5;

FIG. 8 is a section view of the negative-pressure source shown in FIG. 5;

FIG. 17 is a section view of another example of a pump that may be associated with some embodiments of the negative-pressure source;

FIG. 18 is a section view of another example of a pump that may be associated with some embodiments of the negative-pressure source;

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
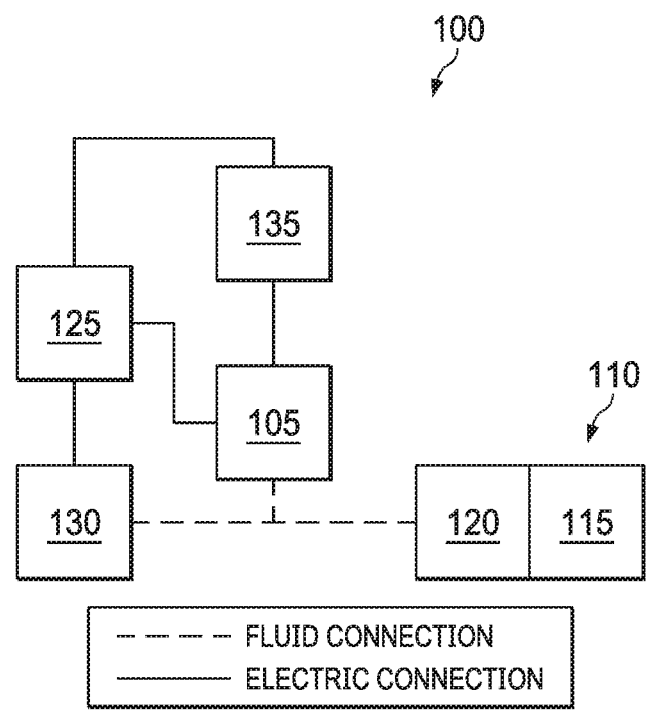
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110 is an example of a distribution component that may be associated with some examples of the therapy system 100. As illustrated in the example of FIG. 1, the dressing 110 may comprise or consist essentially of a tissue interface 115, a cover 120, or both in some embodiments.

The therapy system 100 may also include a regulator or controller, such as a controller 125. Additionally, the therapy system 100 may include sensors to measure operating parameters and provide feedback signals to the controller 125 indicative of the operating parameters. As illustrated in FIG. 1, for example, the therapy system 100 may include a first sensor 130 and a second sensor 135 coupled to the controller 125.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 125 and other components into a therapy unit.

In general, components of the therapy system 100 may be coupled directly or indirectly. For example, the negative-pressure source 105 may be directly coupled to the dressing 110. Coupling may include fluid, mechanical, thermal, electrical, or chemical coupling (such as a chemical bond), or some combination of coupling in some contexts. For example, the negative-pressure source 105 may be electrically coupled to the controller 125 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

A controller, such as the controller 125, may be a microprocessor or computer programmed to operate one or more components of the therapy system 100, such as the negative-pressure source 105. In some embodiments, for example, the controller 125 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 115, for example. The controller 125 is also preferably configured to receive one or more input signals, such as a feedback signal, and programmed to modify one or more operating parameters based on the input signals.

Sensors, such as the first sensor 130 and the second sensor 135, are generally known in the art as any apparatus operable to detect or measure a physical phenomenon or property, and generally provide a signal indicative of the phenomenon or property that is detected or measured. For example, the first sensor 130 and the second sensor 135 may be configured to measure one or more operating parameters of the therapy system 100. In some embodiments, the first sensor 130 may be a transducer configured to measure pressure in a pneumatic pathway and convert the measurement to a signal indicative of the pressure measured. In some embodiments, for example, the first sensor 130 may be a piezo-resistive strain gauge. The second sensor 135 may optionally measure operating parameters of the negative-pressure source 105, such as a voltage or current, in some embodiments. Preferably, the signals from the first sensor 130 and the second sensor 135 are suitable as an input signal to the controller 125, but some signal conditioning may be appropriate in some embodiments. For example, the signal may need to be filtered or amplified before it can be processed by the controller 125. Typically, the signal is an electrical signal, but may be represented in other forms, such as an optical signal.

The tissue interface 115 can be generally adapted to partially or fully contact a tissue site. The tissue interface 115 may take many forms, and may have many sizes, shapes, or thicknesses, depending on a variety of factors, such as the type of treatment being implemented or the nature and size of a tissue site. For example, the size and shape of the tissue interface 115 may be adapted to the contours of deep and irregular shaped tissue sites. Any or all of the surfaces of the tissue interface 115 may have an uneven, coarse, or jagged profile.

In some embodiments, the tissue interface 115 may comprise or consist essentially of a manifold. A manifold in this context may comprise or consist essentially of a means for collecting or distributing fluid across the tissue interface 115 under pressure. For example, a manifold may be adapted to receive negative pressure from a source and distribute negative pressure through multiple apertures across the tissue interface 115, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 115 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 115 may also vary according to needs of a prescribed therapy. The 25% compression load deflection of the tissue interface 115 may be at least 0.35 pounds per square inch, and the 65% compression load deflection may be at least 0.43 pounds per square inch. In some embodiments, the tensile strength of the tissue interface 115 may be at least 10 pounds per square inch. The tissue interface 115 may have a tear strength of at least 2.5 pounds per inch. In some embodiments, the tissue interface 115 may be foam comprised of polyols such as polyester or polyether, isocyanate such as toluene diisocyanate, and polymerization modifiers such as amines and tin compounds. In some examples, the tissue interface 115 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 115 may also vary according to needs of a prescribed therapy. For example, the thickness of the tissue interface may be decreased to reduce tension on peripheral tissue. The thickness of the tissue interface 115 can also affect the conformability of the tissue interface 115. In some embodiments, a thickness in a range of about 5 millimeters to 10 millimeters may be suitable.

The tissue interface 115 may be either hydrophobic or hydrophilic. In an example in which the tissue interface 115 may be hydrophilic, the tissue interface 115 may also wick fluid away from a tissue site, while continuing to distribute negative pressure to the tissue site. The wicking properties of the tissue interface 115 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

In some embodiments, the tissue interface 115 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 115 may further serve as a scaffold for new cell-growth, or a scaffold material may be used in conjunction with the tissue interface 115 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 120 may provide a bacterial barrier and protection from physical trauma. The cover 120 may also be constructed from a material that can reduce evaporative losses and provide a fluid seal between two components or two environments, such as between a therapeutic environment and a local external environment. The cover 120 may comprise or consist of, for example, an elastomeric film or membrane that can provide a seal adequate to maintain a negative pressure at a tissue site for a given negative-pressure source. The cover 120 may have a high moisture-vapor transmission rate (MVTR) in some applications. For example, the MVTR may be at least 250 grams per square meter per twenty-four hours ($g/m^2/24$ hours) in some embodiments, measured using an upright cup technique according to ASTM E96/E96M Upright Cup Method at 38° C. and 10% relative humidity (RH). In some embodiments, an MVTR up to 5,000 $g/m^2/24$ hours may provide effective breathability and mechanical properties.

In some example embodiments, the cover 120 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 120 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber, butyl rubber, ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis, Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inspire 2327 polyurethane films, commercially available from Expopack Advanced Coatings, Wrexham, United Kingdom. In some embodiments, the cover 120 may comprise INSPIRE 2301 having an MVTR (upright cup technique) of 2600 $g/m^2/24$ hours and a thickness of about 30 microns.

An attachment device may be used to attach the cover 120 to an attachment surface, such as undamaged epidermis, a gasket, or another cover. The attachment device may take many forms. For example, an attachment device may be a medically-acceptable, pressure-sensitive adhesive configured to bond the cover 120 to epidermis around a tissue site. In some embodiments, for example, some or all of the cover 120 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In operation, the tissue interface 115 may be placed within, over, on, or otherwise proximate to a tissue site. If the tissue site is a wound, for example, the tissue interface 115 may partially or completely fill the wound, or it may be placed over the wound. The cover 120 may be placed over the tissue interface 115 and sealed to an attachment surface near a tissue site. For example, the cover 120 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 115 in the sealed therapeutic environment can induce macro-strain and micro-strain in the tissue site. Negative pressure can also remove exudate and other fluid from a tissue site, which can be collected in a container (not shown).

In some embodiments, the controller 125 may receive and process data from one or more sensors, such as the first sensor 130. The controller 125 may also control the operation of one or more components of the therapy system 100 to manage the pressure delivered to the tissue interface 115. In some embodiments, controller 125 may include an input for receiving a desired target pressure and may be programmed for processing data relating to the setting and inputting of the target pressure to be applied to the tissue interface 115. In some example embodiments, the target pressure may be a fixed pressure value set by an operator as the target negative pressure desired for therapy at a tissue site and then provided as input to the controller 125. The target pressure may vary from tissue site to tissue site based on the type of tissue forming a tissue site, the type of injury or wound (if any), the medical condition of the patient, and the preference of the attending physician. After selecting a desired target pressure, the controller 125 can operate the negative-pressure source 105 in one or more control modes based on the target pressure and may receive feedback from one or more sensors to maintain the target pressure at the tissue interface 115.

In some embodiments, the controller 125 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 125 can operate the negative-pressure source 105 to cycle between a target pressure and atmospheric pressure. For example, the target pressure may be set at a value of −135 mmHg for a specified period of time (e.g., 5 min), followed by a specified period of time (e.g., 2 min) of deactivation. The cycle can be repeated by activating the negative-pressure source 105 which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time may be a value substantially equal to the initial rise time.

In some example dynamic pressure control modes, the target pressure can vary with time. For example, the target pressure may vary in the form of a triangular waveform, varying between a negative pressure of 50 and 135 mmHg with a rise time set at a rate of +25 mmHg/min. and a descent time set at −25 mmHg/min. In other embodiments of the therapy system 100, the triangular waveform may vary between negative pressure of 25 and 135 mmHg with a rise time set at a rate of +30 mmHg/min and a descent time set at −30 mmHg/min.

In some embodiments, the controller 125 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 125, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 2:
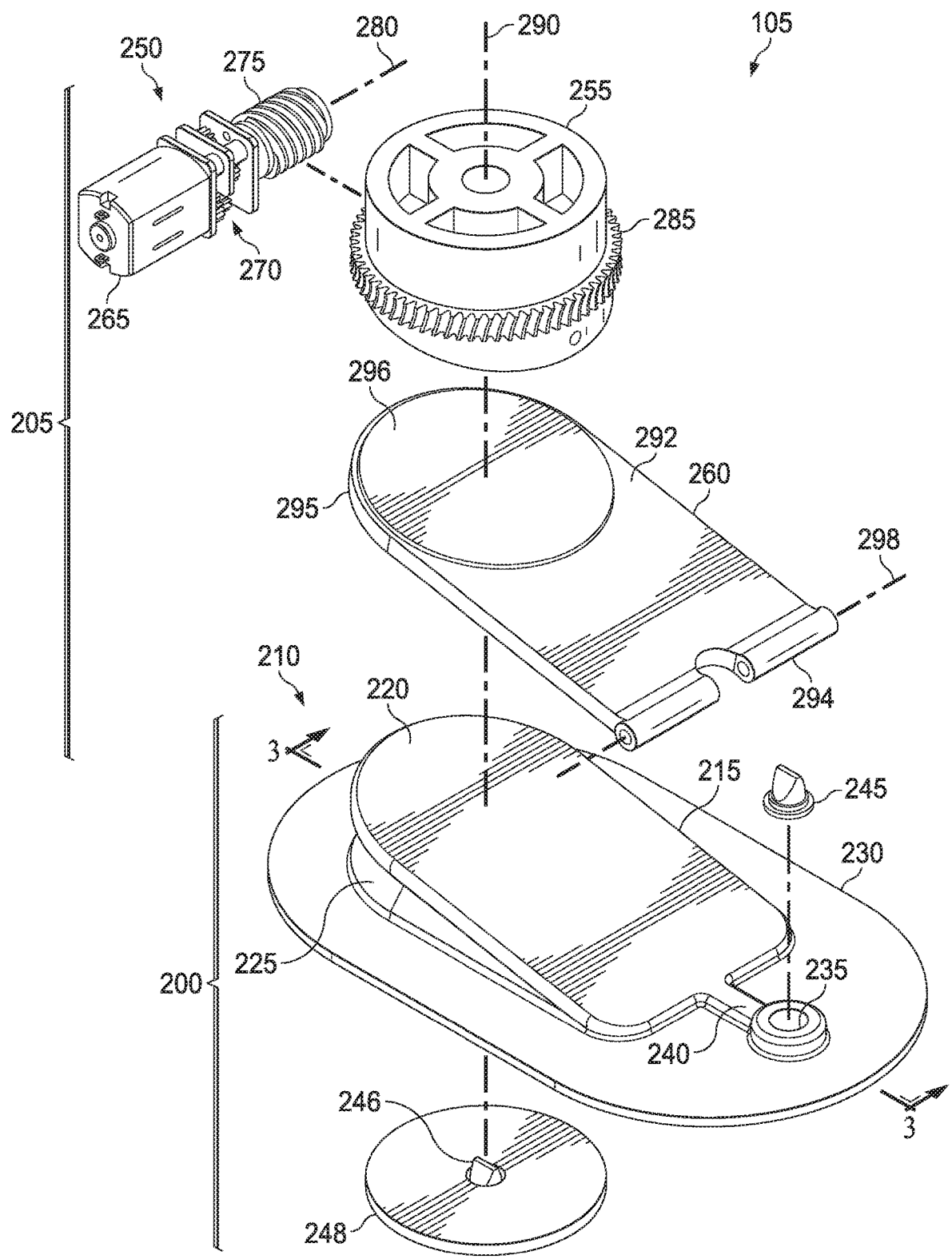
FIG. 2 is an exploded view of a negative-pressure source that may be associated with some embodiments of the therapy system of FIG. 1.

FIG. 2 is an exploded view illustrating additional details of the negative-pressure source 105 that may be associated with some example embodiments of the therapy system 100. In the example embodiment of FIG. 2, the negative-pressure source 105 may comprise a pump 200 and a pump actuator 205. The pump 200 may be a bellows pump.

As shown in the example embodiment of FIG. 2, the pump 200 may comprise a chamber assembly 210 having a chamber wall 215. The chamber wall 215 may include a drive surface 220 and a flexible wall 225 extending downward from the drive surface 220. In some embodiments, the drive surface 220 may have a rectangular shape having rounded corners at a first end and a semi-circle at a second end. As shown in FIG. 2, in some embodiments, the flexible wall 225 may be concertinaed. In some embodiments, the flexible wall 225 may be corrugated. The chamber assembly 210 may further include a base 230 extending outward from the bottom of the chamber wall 215. The base 230 may extend around the entire perimeter of the bottom of the chamber wall 215. The base 230 may be configured to seal the chamber assembly 210 to the cover 120 (not shown). In some embodiments, as shown in FIG. 2, the base 230 may include an exhaust port 235 and an exhaust duct 240. The pump 200 may further include an exhaust valve 245 configured to be located in the exhaust port 235. The pump 200 may further include an intake valve 246. In some embodiments, the intake valve 246 may be retained in a valve holder 248. In some embodiments, the pump 200 may be manually actuated. In some embodiments, the pump 200 may be actuated by the pump actuator 205.

As further shown in FIG. 2, the pump actuator 205 may comprise a motor assembly 250, a cam 255, and a drive plate 260. The motor assembly 250 may include a motor 265, a gear train 270, and a worm 275. The motor 265 may be an electric motor that is electrically coupled with and powered by a source of electrical energy, such as a battery. In some embodiments, the motor 265 may be a DC motor. The gear train 270 may be operatively coupled to the motor 265. The gear train 270 may comprise a plurality of gears to increase the torque of the motor 265. A driveshaft (not shown) may extend from the gear train 270. The worm 275 may be operatively coupled with the driveshaft such that the motor 265 can rotate the worm 275 about a worm axis 280.

In some embodiments, the cam 255 may include a worm gear 285. In some embodiments, the cam 255 and the worm gear 285 may be integrally formed. In some embodiments, the cam 255 and the worm gear 285 may be separate parts that are coupled together. The cam 255 may be configured to rotate about a cam axis of rotation 290. The worm gear 285 may be configured to be driven by the worm 275. Thus rotation of the motor 265 causes the worm 275 to rotate about the worm axis 280 and the worm 275 may engage with the worm gear 285, causing the worm gear 285 to rotate about the cam axis of rotation 290.

In some embodiments, the drive plate 260 may comprise a plate 292 having a first end 294 and a second end 295. As shown in FIG. 2, the first end 294 may be hinged and the second end 295 may be rounded. The plate 292 may be formed of a rigid material and may have a shape similar to that of the drive surface 220 of the chamber assembly 210. A slider disk 296 may be coupled to the plate 292 proximate to the second end 295. The slider disk 296 may be circular in shape and may be formed of a rigid, low-friction material. The cam 255 may be configured to contact the slider disk 296. The low-friction material of the slider disk 296 reduces the friction force on the cam 255, allowing the cam 255 to rotate more easily on the slider disk 296. Additionally, the first end 294 may be rotatably coupled to a housing (not shown). The drive plate 260 may rotate about a hinge axis 298 during operation of the pump actuator 205. As shown in FIG. 2, the drive plate 260 may be located between the cam 255 and the chamber assembly 210.

Figure 3:
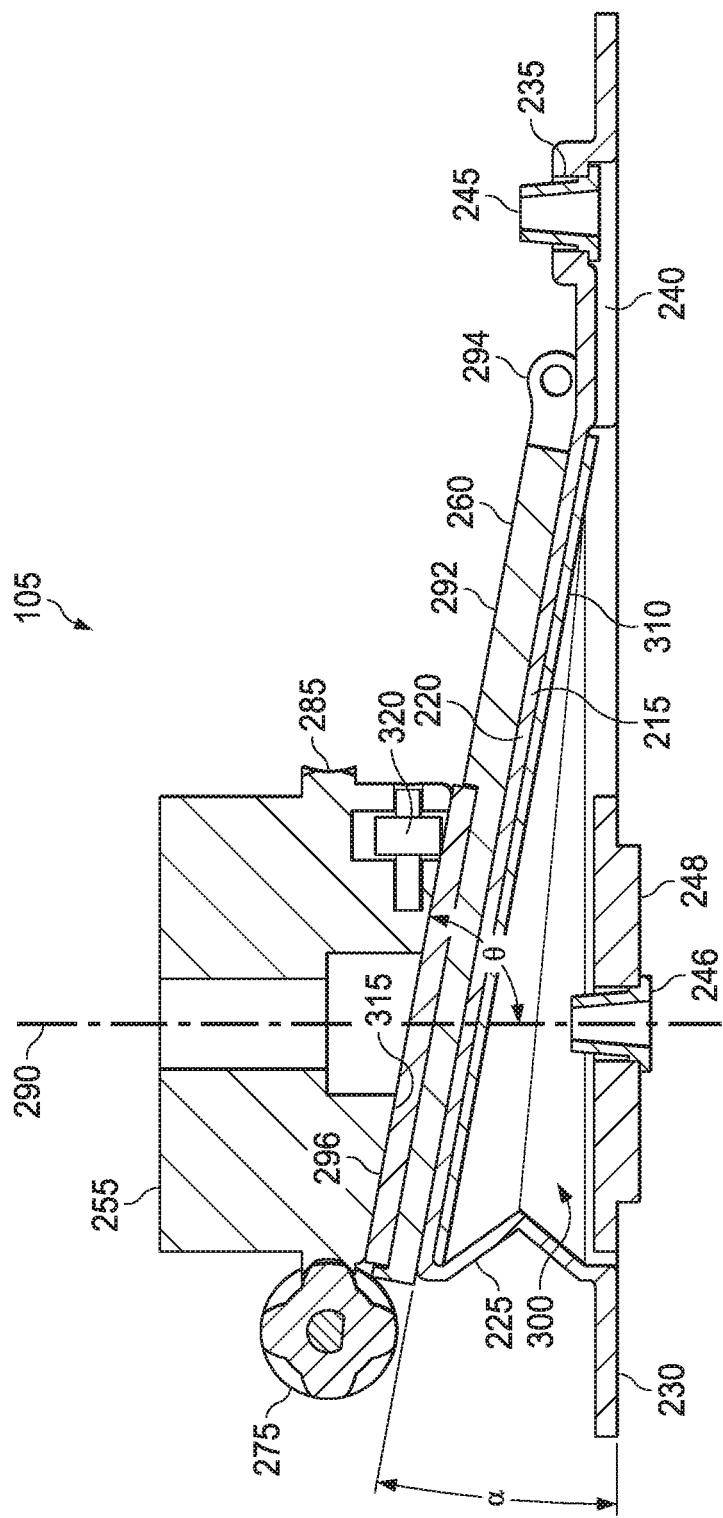
FIG. 3 is a section view of the negative-pressure source shown in FIG. 2.

FIG. 3 is a section view of the negative-pressure source 105 shown in FIG. 2, as assembled, taken along line 3-3. As shown in FIG. 3, the chamber wall 215 may define a pump chamber 300. In some embodiments, the drive surface 220 and the flexible wall 225 may define the pump chamber 300. The pump chamber 300 may be configured to be fluidly coupled with the tissue interface 115 (not shown). The exhaust duct 240 may fluidly couple the pump chamber 300 to the exhaust port 235 and the exhaust valve 245. The exhaust valve 245 may be configured to be located in the exhaust port 235. The exhaust valve 245 may only permit one-way fluid flow out of the pump chamber 300. In some embodiments, for example, the exhaust valve 245 may be a duckbill valve. The intake valve 246 may be configured to be fluidly coupled with the pump chamber 300. In some embodiments, the intake valve 246 may only permit one-way fluid flow into the pump chamber 300. In some embodiments, for example, the intake valve 246 may be a duckbill valve.

In FIG. 3, the pump 200 is shown in its unactuated position. In the unactuated position, the drive surface 220 may be oriented at a positive angle α with respect to the base 230. In some embodiments, in the unactuated position, the drive surface 220 may be at an angle α in a range of about 10 degrees to about 45 degrees with respect to the base 230. In some embodiments, in the unactuated position, the drive surface 220 may be at an angle α in a range of about 20 degrees to about 30 degrees with respect to the base 230. In other embodiments, in the unactuated position, the drive surface 220 may at an angle α of about 30 degrees with respect to the base 230. In other embodiments, the drive surface 220 may at an angle α of about 15 degrees with respect to the base 230. Accordingly, the pump chamber 300 may have a wedge shape when viewed from the side.

In some embodiments, at least the flexible wall 225 of the chamber wall 215 may be formed of a resilient material. In some embodiments, for example, the drive surface 220, the flexible wall 225, and the base 230 may all be formed of a resilient material. In some embodiments, the drive surface 220, flexible wall 225, and base 230 may be integrally formed. In other embodiments, the drive surface 220 may be more rigid than the flexible wall 225. For example, the drive surface 220 may be substantially rigid such that it does not bend or yield during operation of the pump 200. As additionally shown in FIG. 3, in some embodiments, the pump 200 may further include a plate 310 coupled to the underside of the drive surface 220, within the pump chamber 300. The plate 310 may provide additional stiffness to the drive surface 220.

Additionally, as shown in FIG. 3, the cam 255 of the pump actuator 205 may include a working surface 315. In some embodiments, the cam 255 may be an end or face cam. In some embodiments, the working surface 315 may have a wedge shape. In some embodiments, the working surface 315 may be have a curved or arcuate surface. In some embodiments, as shown in FIG. 3, the working surface 315 may be configured to contact the slider disk 296 of the drive plate 260. FIG. 3 shows the cam 255 in the unactuated position. When the cam 255 is in the unactuated position, the working surface 315 of the cam 255 may have a positive angle that is equal to the positive angle of the drive surface 220 of the chamber assembly 210. Stated another way, when in the unactuated position, the working surface 315 may be parallel to the drive surface 220 of the chamber assembly 210.

In some embodiments, the working surface 315 may be at an angle Θ in a range of about 45 degrees to about 80 degrees with respect to the cam axis of rotation 290. In some embodiments, the working surface 315 may be at an angle Θ in a range of about 60 degrees to about 70 degrees with respect to the cam axis of rotation 290. In other embodiments, for example, the working surface 315 may be at an angle Θ of about 60 degrees with respect to the cam axis of rotation 290. In other embodiments, the working surface 315 may be at an angle Θ of about 75 degrees with respect to the cam axis of rotation 290. In some embodiments, the cam axis of rotation 290 may be perpendicular to the base 230.

In some embodiments, as further shown in FIG. 3, the cam 255 may further include a roller bearing 320 located at the apex of the working surface 315. The roller bearing 320 may further reduce the friction force on the cam 255, allowing the cam 255 to rotate more easily on the slider disk 296. In some embodiments, the roller bearing 320 may extend slightly beyond the working surface 315 of the cam 255.

Although not shown in FIG. 2 or FIG. 3, the components of the pump actuator 205 may be enclosed within a housing. The housing may operatively retain the motor assembly 250, the cam 255, and the drive plate 260. The motor 265 may be fixed within the housing. The cam 255 may be rotatably fixed within the housing such that the cam 255 can rotate about the cam axis of rotation 290. Additionally, the drive plate 260 may be rotatably fixed within the housing such that the drive plate 260 can rotate about the hinge axis 298.

In operation, when the motor 265 of the pump actuator 205 receives electrical power, the motor 265 rotates the gears of the gear train 270 thereby causing the driveshaft to rotate the worm 275 about the worm axis 280. Teeth of the worm 275 are engaged with teeth of the worm gear 285 and transfer rotation of the worm 275 into rotation of the worm gear 285 and cam 255, causing the cam 255 to rotate about the cam axis of rotation 290. The cam 255 may rotate 360 degrees from the unactuated position and the actuated position. As the cam 255 rotates from the unactuated position to the actuated position, the working surface 315 can engage the slider disk 296 of the drive plate 260 to exert a force on the drive plate 260 toward the base 230. The drive plate 260 pushes on the drive surface 220 of the chamber assembly 210, decreasing the angle α between the drive surface 220 and the base 230. The drive surface 220 is then at the actuated position. This causes the pump chamber 300 to be compressed and evacuates fluid out of the pump chamber 300 through the exhaust valve 245. As the cam 255 rotates from the actuated position to the unactuated position, the force on the drive plate 260 is removed, and the angle α between the drive surface 220 and the base 230 increases. The pump chamber 300 expands, pulling fluid into the pump chamber 300 through the intake valve 246 and returning to an unactuated position. The drive surface 220 is then at the unactuated position. The resilient nature of the flexible wall 225 may push upward on the drive surface 220, returning the drive surface 220 to its unactuated position. In embodiments where the pump 200 is power actuated, the resilient nature of the flexible wall 225 may reduce energy consumption. For example, battery drain may be reduced and motor size may be reduced. The pumping action continues for as long as power is supplied to the motor 265. This cyclic compression and expansion of the pump chamber 300 creates a negative pressure in the pump chamber 300, wherein this negative pressure may be supplied to a tissue interface to decrease the pressure in the tissue interface.

Figure 4:
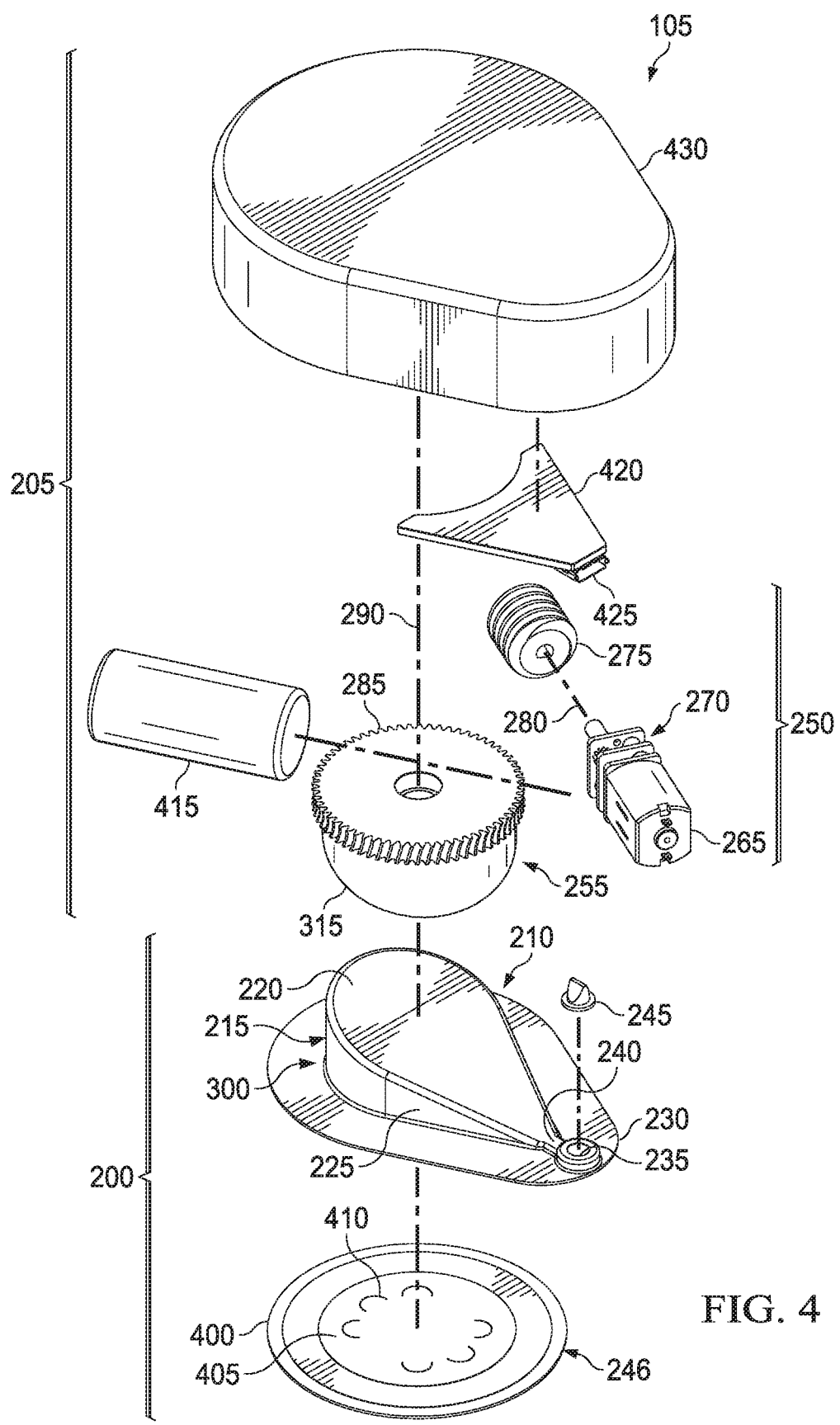
FIG. 4 is an exploded view of a another example of a negative-pressure source that may be associated with some embodiments of the therapy system of FIG. 1.

FIG. 4 is an exploded view of another example of the negative-pressure source 105 that may be associated with some embodiments of the therapy system 100. As shown in FIG. 4, in some embodiments, the intake valve 246 may be a flat valve. The intake valve 246 may be circular with a perimeter sealing region 400 surrounding a central valve region 405 having one or more valves 410. The perimeter sealing region 400 may be fluidly sealed to the base 230 of the chamber assembly 210. In some embodiments, the one or more valves 410 may be flat valves that only permit fluid flow in the direction of the pump chamber 300. In some examples, the intake valve 246 may be a flat valve such as a FLEXIS™ valve available from CCL Industries of Framingham, Massachusetts.

As further shown in FIG. 4, in some embodiments the drive surface 220 and the pump chamber 300 of the chamber assembly 210 may have a teardrop shape when viewed from the top. In some embodiments, the narrow end of the drive surface 220 may be coincident with the base 230 and the wider end of the drive surface 220 may be spaced a non-zero distance away from the base 230. As shown in FIG. 4, in some embodiments, the working surface 315 of the cam 255 may be configured to directly contact and drive the drive surface 220 of the chamber assembly 210.

The pump actuator 205 may include the cam 255, the motor assembly 250 having the motor 265, gear train 270 and the worm 275, a battery 415, and a printed circuit board 420. In some embodiments, a housing 430 may enclose the cam 255 and the motor assembly 250. The battery 415, printed circuit board 420, and the motor 265 may all be electrically coupled. The battery 415 may supply electrical energy to the motor 265. The printed circuit board 420 may include various electrical elements and circuitry to control the operation of the motor 265. Furthermore, the pump actuator 205 may include a port 425, such as for example, a micro-USB port, or a USB-C port, for supplying electrical power to the battery 415 and/or the motor 265 and/or to transmit data between the pump actuator 205 and a separate device (e.g., a computer, smartphone, tablet, etc.). The pump actuator 205 may further include a switch (not shown) for turning the motor ON and OFF. The components of the pump actuator 205 may be housed in the housing 430.

Figure 5:
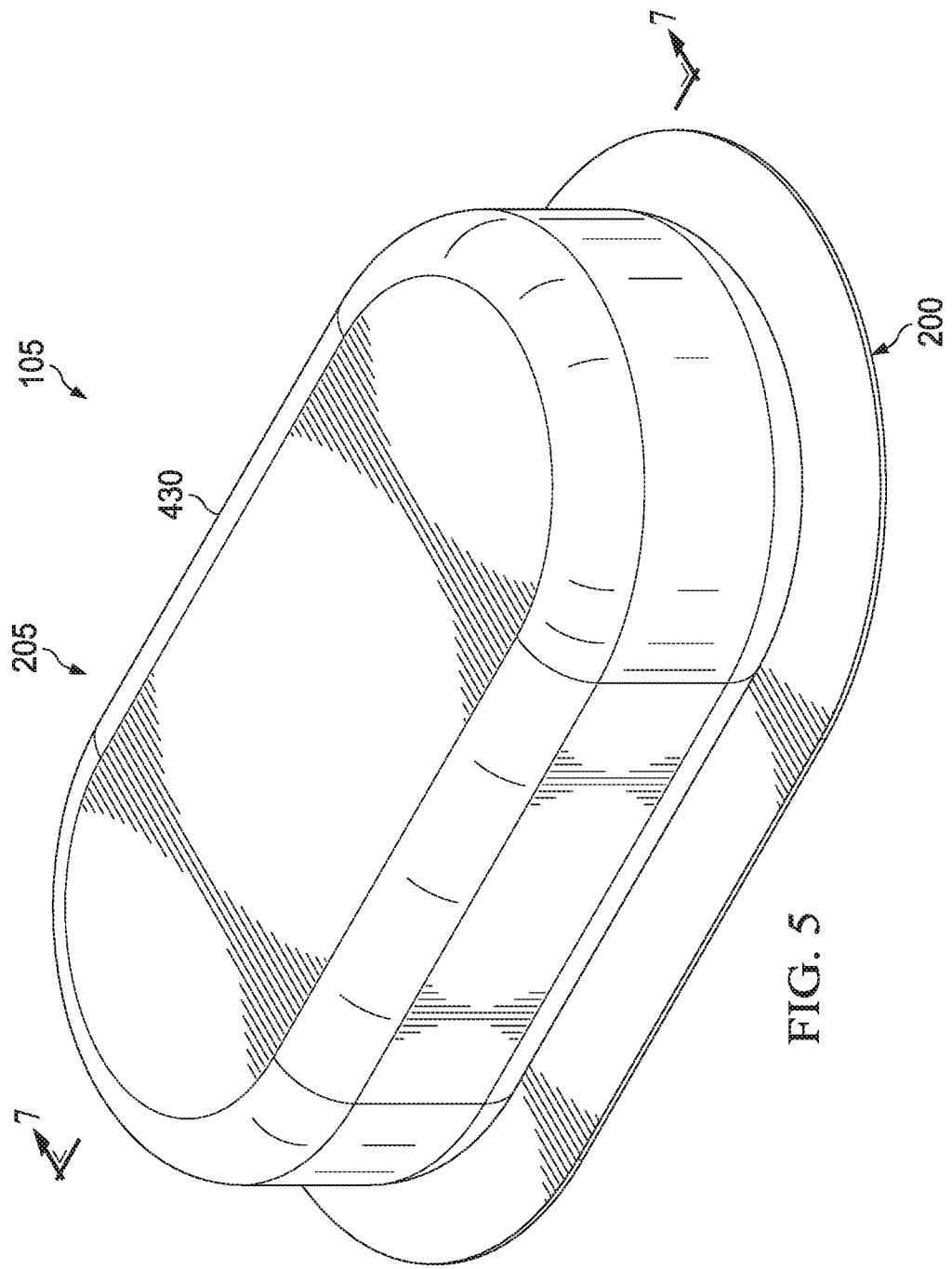
FIG. 5 is an isometric view of another example of a negative-pressure source that may be associated with some example embodiments of the therapy system of FIG. 1.

FIG. 5 is an isometric view of another example of the negative-pressure source 105 that may be associated with some example embodiments of the therapy system 100. As shown in FIG. 5, the housing 430 of the pump actuator 205 may have a generally stadium shape.

Figure 6:
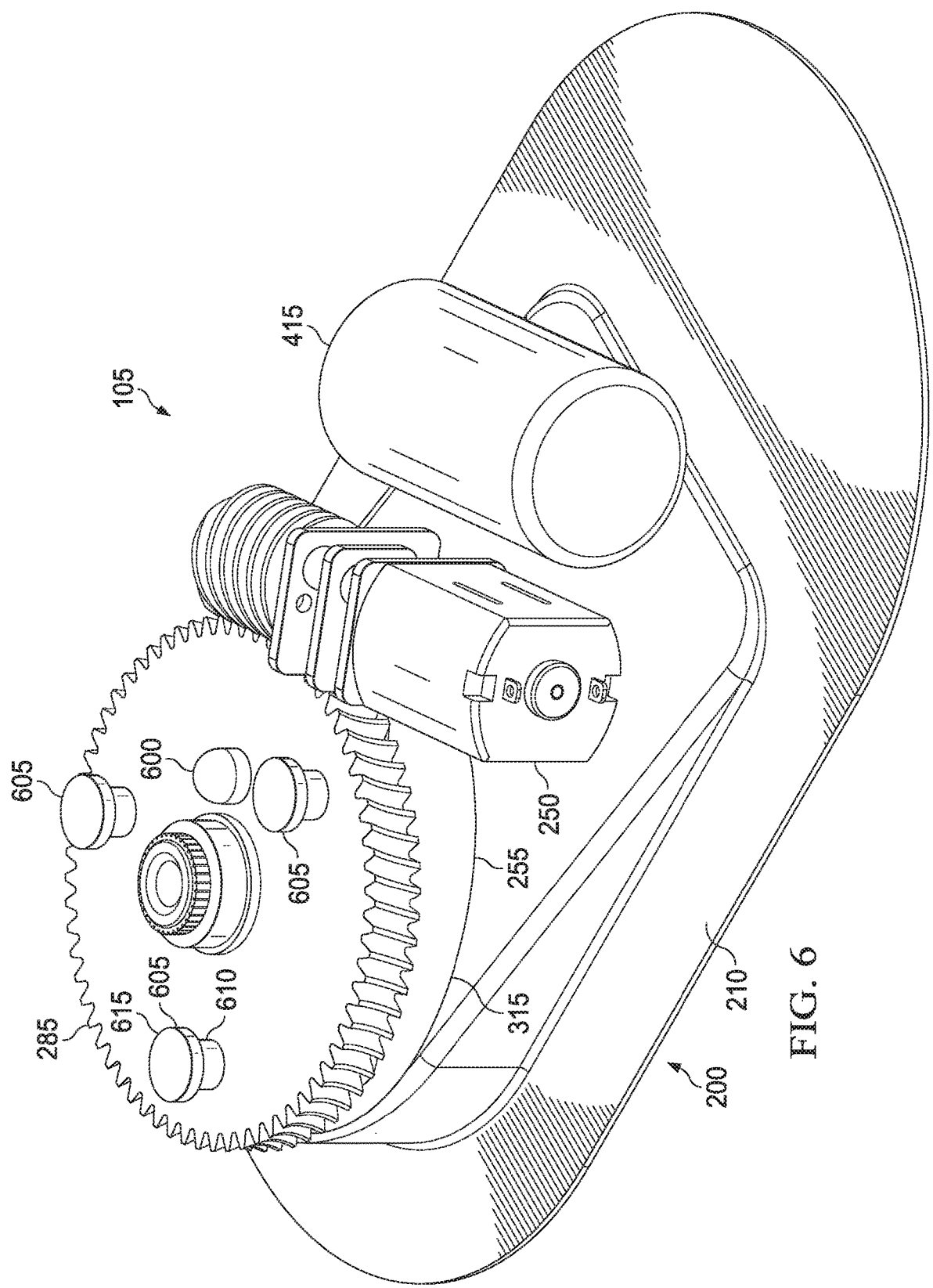
FIG. 6 is an isometric view of the negative-pressure source shown in FIG. 5.

FIG. 6 is an isometric view of the negative-pressure source 105 shown in FIG. 5. The housing 430 of the pump actuator 205 is not shown in FIG. 6 so that the battery 415, the motor assembly 250, the worm gear 285, and the cam 255 can be readily viewed. In the example embodiment shown in FIG. 6, the cam 255 and the worm gear 285 are separate components that are coupled together, and the cam 255 can move linearly with respect to the worm gear 285. The cam 255 may include a cam follower 600 and three retention members 605 extending upward from the cam 255 away from the working surface 315. The worm gear 285 may include four holes through which the cam follower 600 and the three retention members 605 can extend. The cam follower 600 may terminate in a hemispherical tip. The retention members 605 may comprise cylindrical rods 610 and may terminate with stops 615. The stops 615 may comprise cylindrical heads having a diameter larger than the diameter of the holes in the worm gear 285. The stops 615 of the retention members 605 limit the linear movement of the cam 255 downward away from the worm gear 285. Three retention members 605 are shown; however in some embodiments, for example, fewer or greater retention members 605 may be included. In some embodiments, the retention members 605 may two comprise curved walls that are configured to extend through two curved slots in the worm gear 285.

FIG. 7 is a section view of the negative-pressure source 105 shown in FIG. 5 taken along line 7-7 illustrating the pump actuator 205 in the unactuated position. In the example embodiment of FIG. 7, the pump actuator 205 may include a shaft 700 about which the worm gear 285 and the cam 255 are configured to rotate. The housing 430 of the pump actuator 205 may include a stationary cam 705 located above the worm gear 285. The stationary cam 705 may include a stationary working surface 710. The working surface may be at positive angle with respect to the cam axis of rotation 290. For example, in some embodiments, the stationary working surface 710 may be at an angle β in a range of about 45 degrees to about 80 degrees with respect to the cam axis of rotation 290. In some embodiments, for example, the stationary working surface 710 may be at an angle β in a range of about 60 degrees to about 70 degrees with respect to the cam axis of rotation 290. In other embodiments, for example, the stationary working surface 710 may at an angle β of about 60 degrees with respect to the cam axis of rotation 290. In other embodiments, for example, the stationary working surface 710 may at an angle β of about 75 degrees with respect to the cam axis of rotation 290. In some embodiments, the stationary cam 705 may have a wedge or tapered shape when viewed from the side. In other embodiments, the stationary working surface 710 of the stationary cam 705 may have a curved or arcuate surface.

FIG. 8 is a section view of the negative-pressure source 105 shown in FIG. 5 taken along line 7-7 illustrating the pump actuator 205 in the actuated position. As the worm gear 285 is rotated, the cam 255 rotates about the cam axis of rotation 290 (as shown by arrow A) and moves in the direction of the cam axis of rotation 290 (along arrow B). Specifically, the rotation of the worm gear 285 may be transmitted to the cam 255 by the retention members 605 so that the cam 255 can rotate from the unactuated position to the actuated position. The retention members 605 are configured to prevent relative rotation between the cam 255 and the worm gear 285. At the same time, the cam follower 600 rides along the stationary working surface 710 of the stationary cam 705, and due to the angle of the stationary working surface 710, the cam follower 600 is pushed downward. This in turn, pushes the cam 255 downward, which pushes the drive surface 220 of the chamber assembly 210 downward, compressing the pump chamber 300. The retention members 605 may aid in aligning the cam 255 so that it can translate along the cam axis of rotation 290. Additionally, the shaft 700 may also aid in aligning the cam 255. Along with the retention members 605, the shaft 700 may reduce or eliminate binding of the cam 255 during operation of the pump actuator 205. As the cam 255 is rotated, the working surface 315 of the cam 255 also pushes the drive surface 220 of the chamber assembly 210 downward, compressing the pump chamber 300. Thus, the drive surface 220 of the chamber assembly 210 may be pushed downward by both downward movement of the cam 255 and the rotation of the working surface 315 of the cam 255. When the pump actuator 205 reaches the actuated position, the stops 615 of the retention members 605 prevent further translation of the cam 255 downward along the cam axis of rotation 290.

Figure 9:
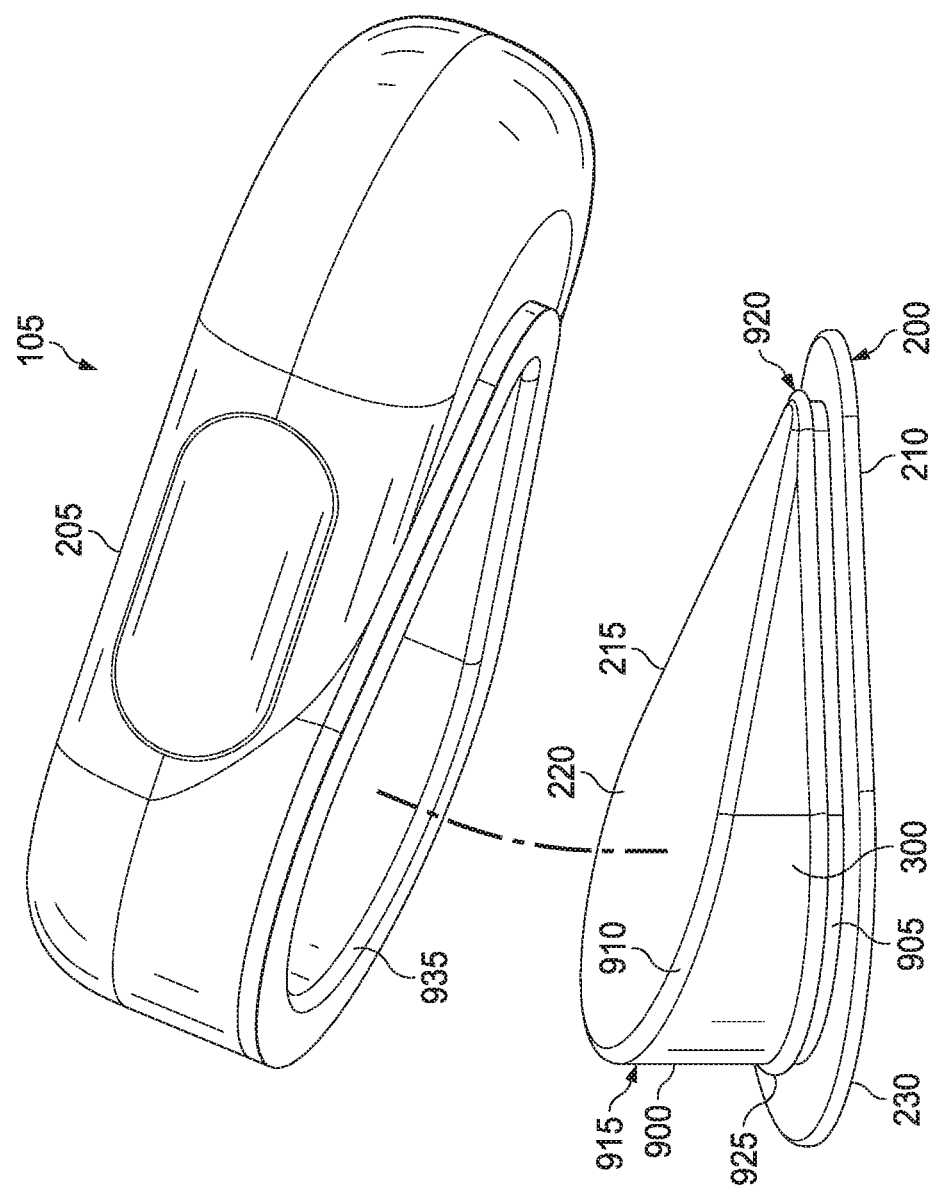
FIG. 9 is an exploded view of another example of a negative-pressure source that may be associated with some embodiments of the therapy system of FIG. 1.

FIG. 9 is an exploded view of another example of the negative-pressure source 105. In the example embodiment of FIG. 9, the chamber wall 215 of the chamber assembly 210 may comprise a perimeter wall 900 extending upward and having a bottom end 905 and a top end 910. The drive surface 220 may be coupled to the top end 910 of the perimeter wall 900. The perimeter wall 900 and the drive surface 220 may define the pump chamber 300. The base 230 may extend radially outward from the bottom end 905 of the perimeter wall 900. The perimeter wall 900 may have a first end 915 and a second end 920, wherein the second end 920 is shorter than the first end 915, such that the drive surface 220 is oriented at a positive angle with respect to the base 230. The chamber assembly 210 may further include an attachment device 925. In some embodiments, the attachment device 925 may comprise or consist essentially of a ridge extending around the perimeter of the perimeter wall 900. In some embodiments, the ridge may be proximate the bottom end 905 of the perimeter wall 900. In some embodiments, the ridge may be about 1 millimeter to about 5 millimeters from the bottom end 905 of the perimeter wall 900. In some embodiments, for example, the ridge may be proximate the drive surface 220 at the second end 920. Additionally, the pump actuator 205 may include a mating element 935, such as a recess. The mating element 935 may cooperate with the attachment device 925 to secure the pump actuator 205 to the chamber assembly 210. For example, the ridge on the pump 200 may be received in and held by the recess on the pump actuator 205.

Figure 10:
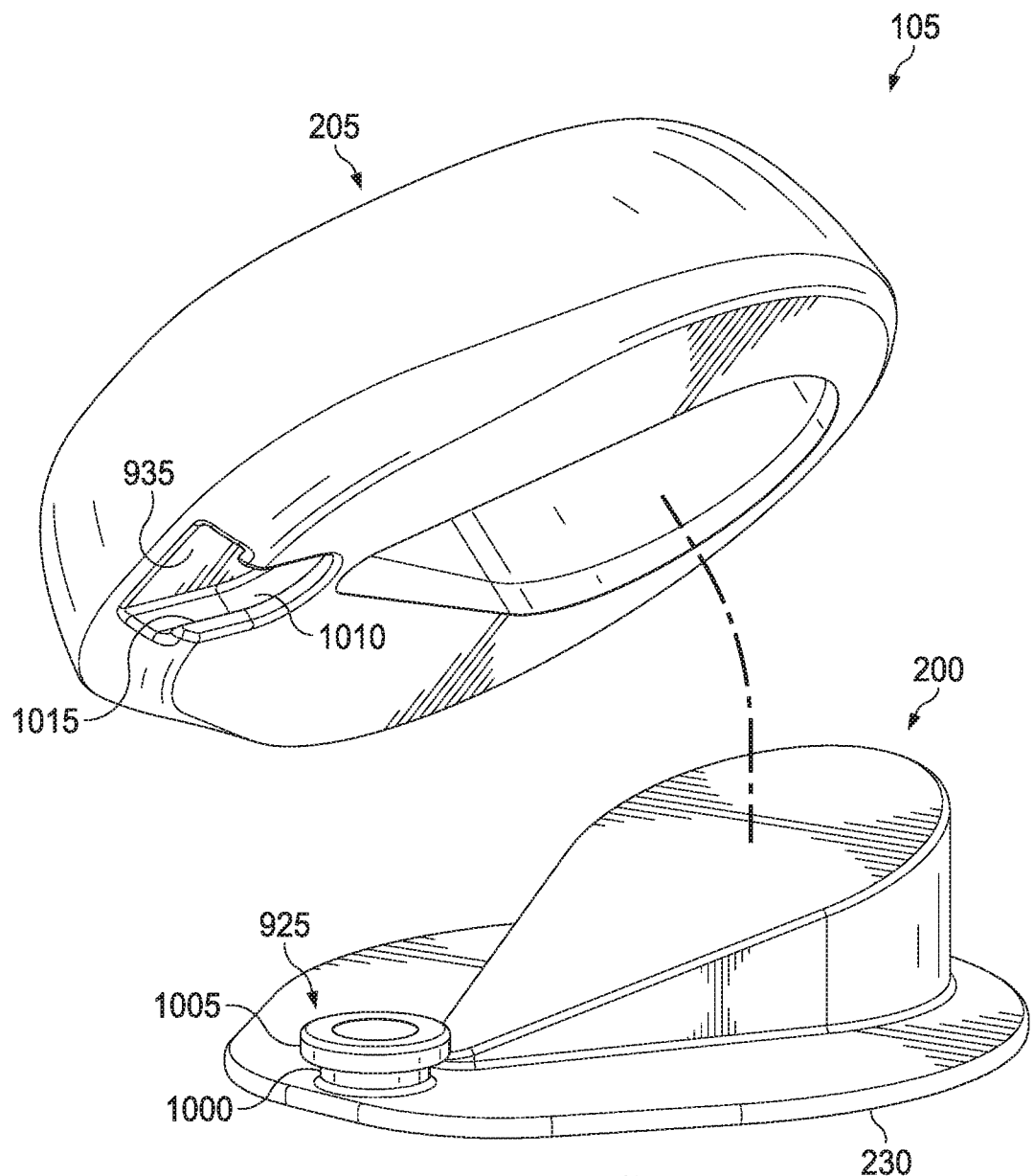
FIG. 10 is an exploded view of another example of a negative-pressure source that may be associated with some embodiments of the therapy system of FIG. 1.

FIG. 10 is an exploded view of another example of the negative-pressure source 105. The attachment device 925 on the pump 200 may include a cylinder 1000 extending upward from the base 230 with a head 1005 at the top of the cylinder 1000. The head 1005 may have a larger diameter than the cylinder 1000. The mating element 935 on the pump actuator 205 may include a T-shaped slot 1010 which may be configured to receive the head 1005 and cylinder 1000 of the attachment device 925. The horizontal portion of the T-shaped slot 1010 may be wide enough to receive the head 1005 of the attachment device 925 while the vertical portion of the T-shaped slot 1010 may be narrower than the horizontal portion of the T-shaped slot 1010. The vertical portion of the T-shaped slot 1010 is wide enough to receive the cylinder 1000 of the attachment device 925. The width difference of the T-shaped slot forms a shoulder 1015 in the pump actuator 205 upon which the bottom of the head 1005 of the attachment device 925 may contact when the pump actuator 205 is properly attached to the pump 200. This contact prevents the pump actuator 205 from lifting off from the pump 200.

Figure 11:
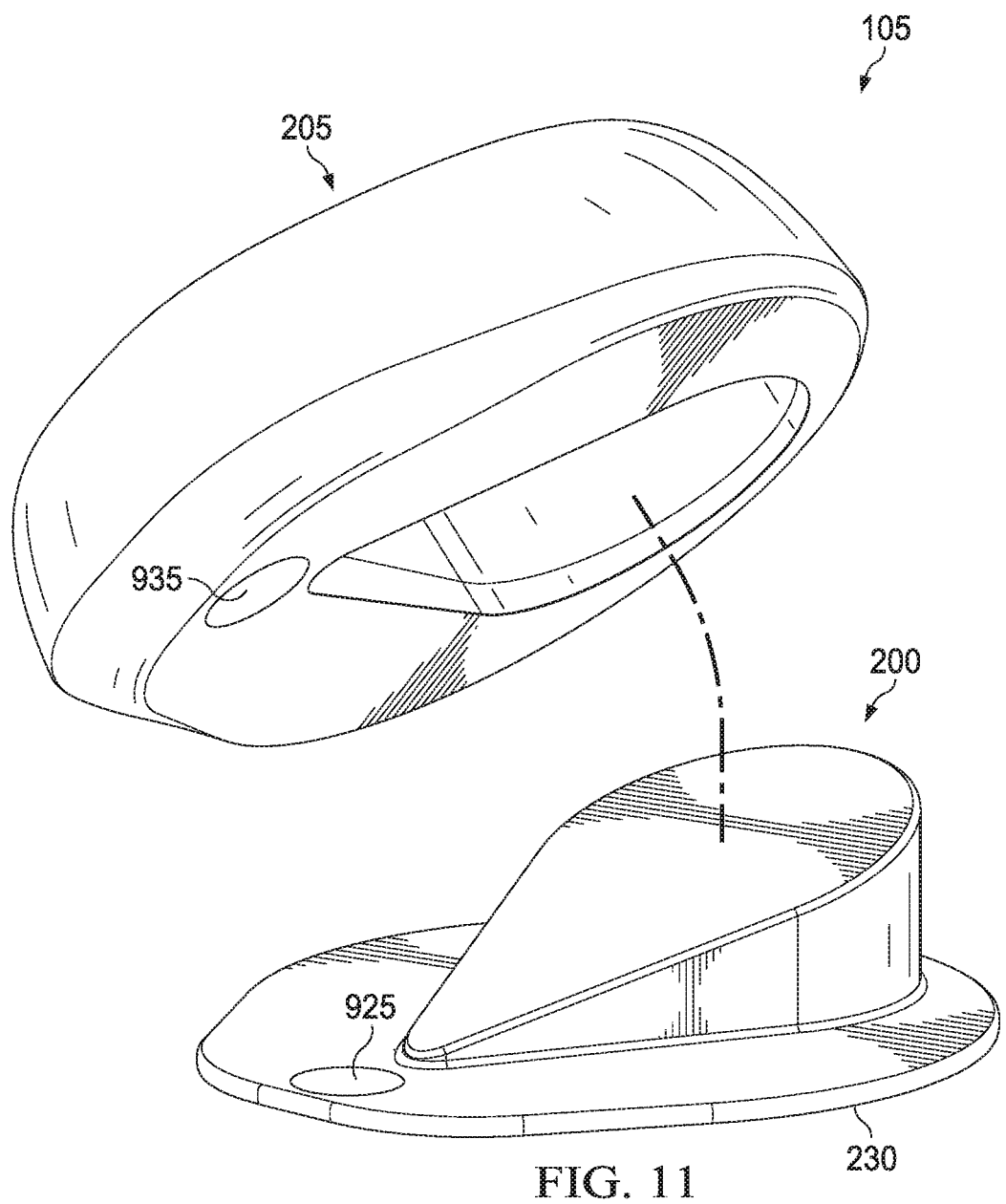
FIG. 11 is an exploded view of another example of a negative-pressure source that may be associated with some embodiments of the therapy system of FIG. 1.

FIG. 11 is an exploded view of another example of the negative-pressure source 105. The attachment device 925 on the pump 200 may include a ferrous metal plate in the base 230. The mating element 935 on the pump actuator 205 may include a magnet. The pump actuator 205 may be held onto the pump 200 by the magnetic force of the magnet. In some embodiments, the magnet may be located in the base 230 and the ferrous metal plate may be located in the pump actuator 205. In some embodiments, both the pump actuator 205 and the pump 200 may be provided with magnets, wherein the polarities of the magnets may be opposed so as to attract the pump actuator 205 to the pump 200. The magnetic force may prevent the pump actuator 205 from lifting off from the pump 200.

Figure 12:
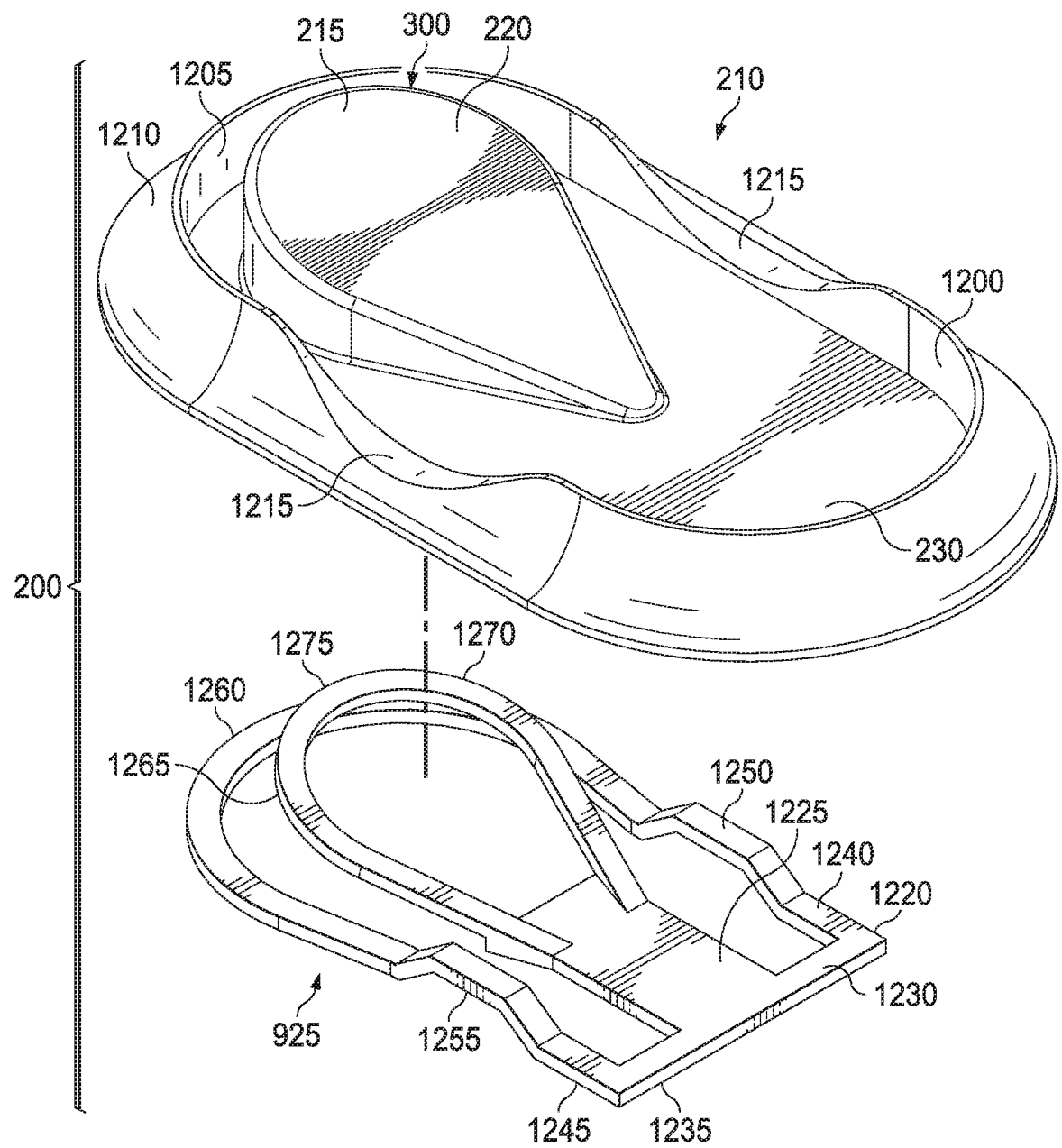
FIG. 12 is an exploded view of an example of a pump that may be associated with some embodiments of the negative-pressure source.

FIG. 12 is an exploded view of an example of the pump 200 that may be associated with some embodiments of the negative-pressure source 105. A wall 1200 may extend away from the base 230 of the chamber assembly 210. As shown in FIG. 12, the wall 1200 may be located a distance inward from the perimeter of the base 230. The wall 1200 may have an inner side 1205 and an outer side 1210. In some examples, the inner side 1205 may be flat, and the outer side 1210 may be curved or filleted. Additionally, as shown, the wall 1200 may have two lower portions 1215.

As further shown in FIG. 12, the attachment device 925 may include a frame 1220. In some embodiments, the frame 1220 includes a base portion 1225. The base portion 1225 may be rectangular. A first wing 1230 may extend outward from the base portion 1225 and a second wing 1235 may extend outward from the base portion 1225 opposite the first wing 1230. A first arm 1240 may extend from the first wing 1230 and a second arm 1245 may extend from the second wing 1235. A first bridge 1250 may extend from the first arm 1240 and a second bridge 1255 may extend from the second arm 1245. An arch 1260 may extend from the first bridge 1250 and may connect to the second bridge 1255. The base portion 1225, the first wing 1230, the second wing 1235, the first arm 1240, the second arm 1245, and the arch 1260 may all be located in a first plane. The first bridge 1250 and the second bridge 1255 may be located in a second plane above the first plane. That is, the first bridge 1250 and the second bridge 1255 may extend above the base portion 1225, the first wing 1230, the second wing 1235, the first arm 1240, the second arm 1245, and the arch 1260.

As further shown in FIG. 12, the frame 1220 may further include a biasing element 1265. The biasing element 1265 may comprise a cantilever spring 1270 extending upward at a positive angle with respect to the base portion 1225. The cantilever spring 1270 may include an arch 1275 extending upward at an angle from the base portion 1225. The cantilever spring 1270 spring may have a shape that corresponds to the shape of the chamber wall 215. For example, the cantilever spring 1270 may be teardrop shaped.

In some embodiments, the frame 1220 may be stamped from a single piece of sheet metal. For example, the frame 1220 may be punched from a piece of sheet metal and then the biasing element 1265 may be folded upward and the first bridge 1250 and the second bridge 1255 may be pushed upward using a one- or two-step forming process. In other embodiments, for example, the frame 1220 may be formed from a rigid plastic.

Figure 13:
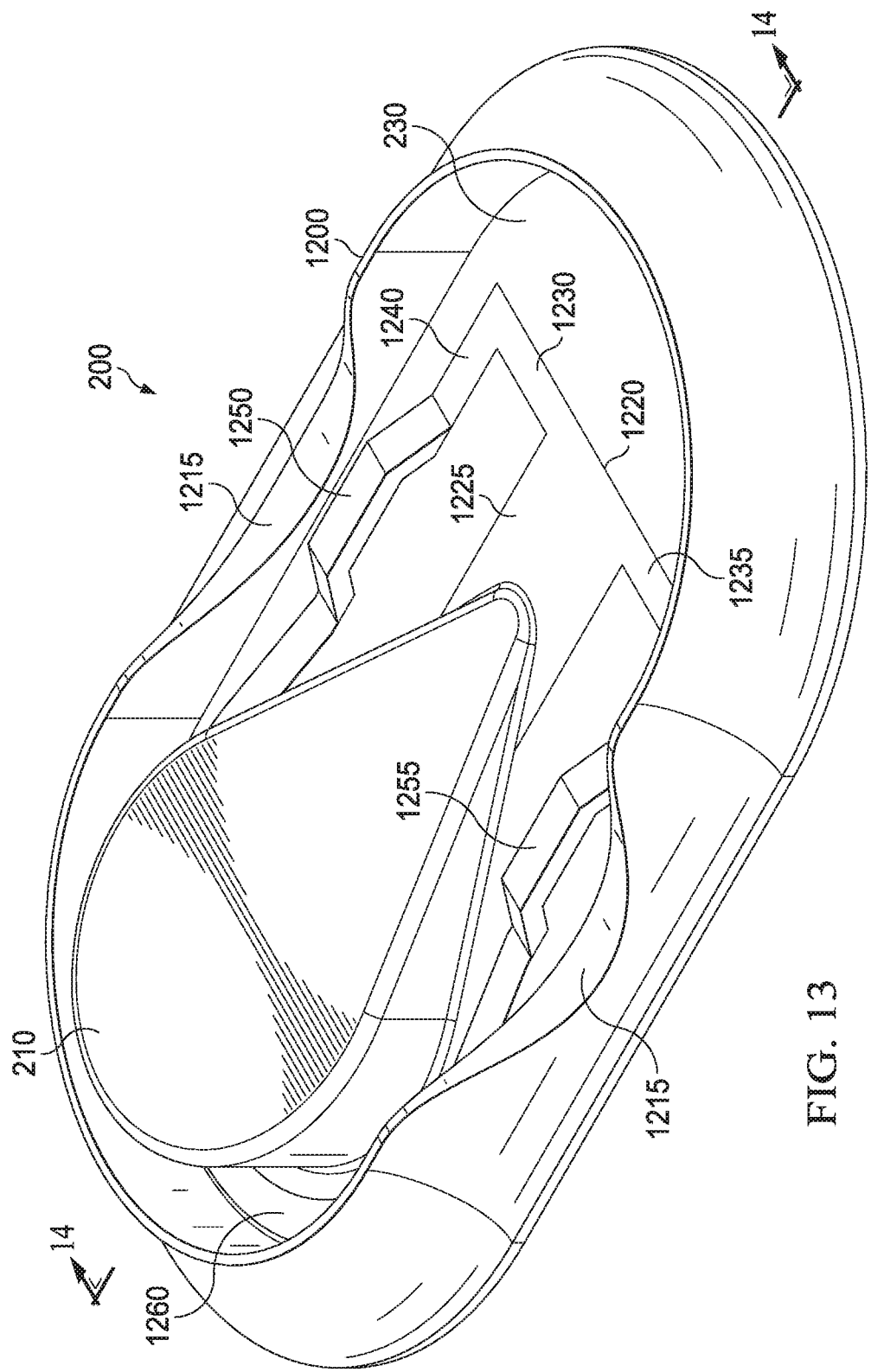
FIG. 13 is an assembled view of the pump shown in FIG. 12.

FIG. 13 is an assembled view of the pump 200 shown in FIG. 12. The base portion 1225, the first wing 1230, the second wing 1235, the first arm 1240, the second arm 1245 (not visible in FIG. 12), and the arch 1260 may all be located in the base 230 of the chamber assembly 210. In some embodiments, the base 230 of the chamber assembly 210 may be overmolded onto the frame 1220. In other embodiments, for example, the frame 1220 may be heatstaked to the base 230 of the chamber assembly 210. In some embodiments, the base portion 1225, the first wing 1230, the second wing 1235, the first arm 1240, the second arm 1245, and the arch 1260 may all be located below the base 230 of the chamber assembly 210.

As further shown in FIG. 13, the first bridge 1250 and the second bridge 1255 may extend above the base 230 of the chamber assembly 210. The first bridge 1250 and the second bridge 1255 may additionally be located proximate the lower portions 1215 of the wall 1200 of the chamber assembly 210.

Figure 14:
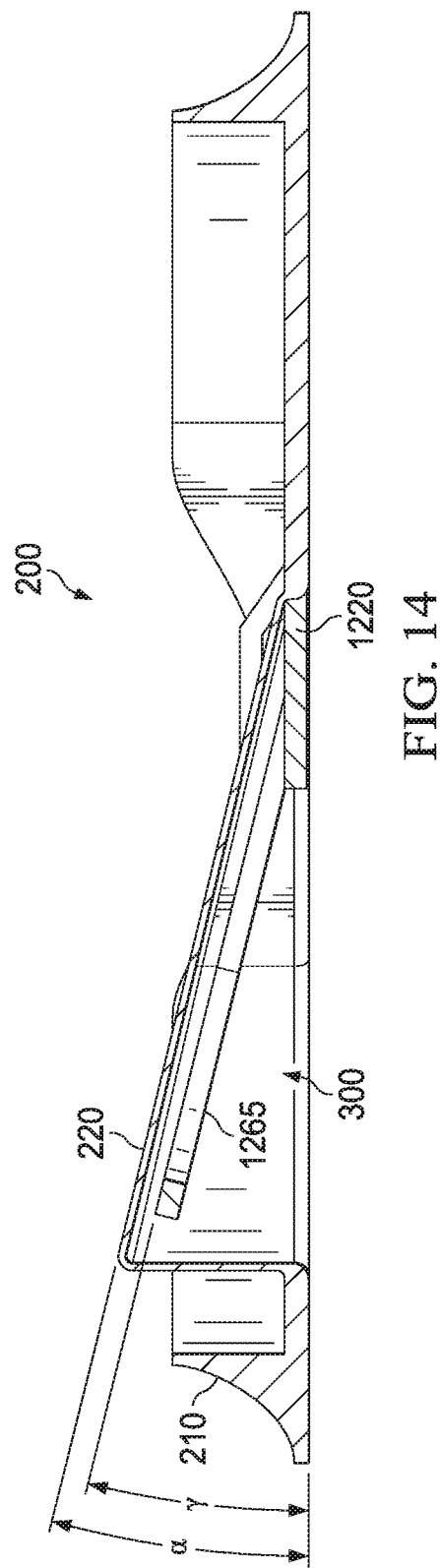
FIG. 14 is a section view of the pump shown in FIG. 13.

FIG. 14 is a section view of the pump 200 shown in FIG. 13 taken along line 14-14. As shown in FIG. 14, the biasing element 1265 may be located below the drive surface 220. The biasing element 1265 may be configured to bias the drive surface 220 upward. Thus, the biasing element 1265 may be configured to return the pump chamber 300 to an unactuated position from the actuated position. The biasing element 1265 may thus bias the pump chamber 300 to an expanded state. As shown in the example FIG. 14, the angle γ of the biasing element 1265 may be equal to the angle α of the drive surface 220.

Figure 15:
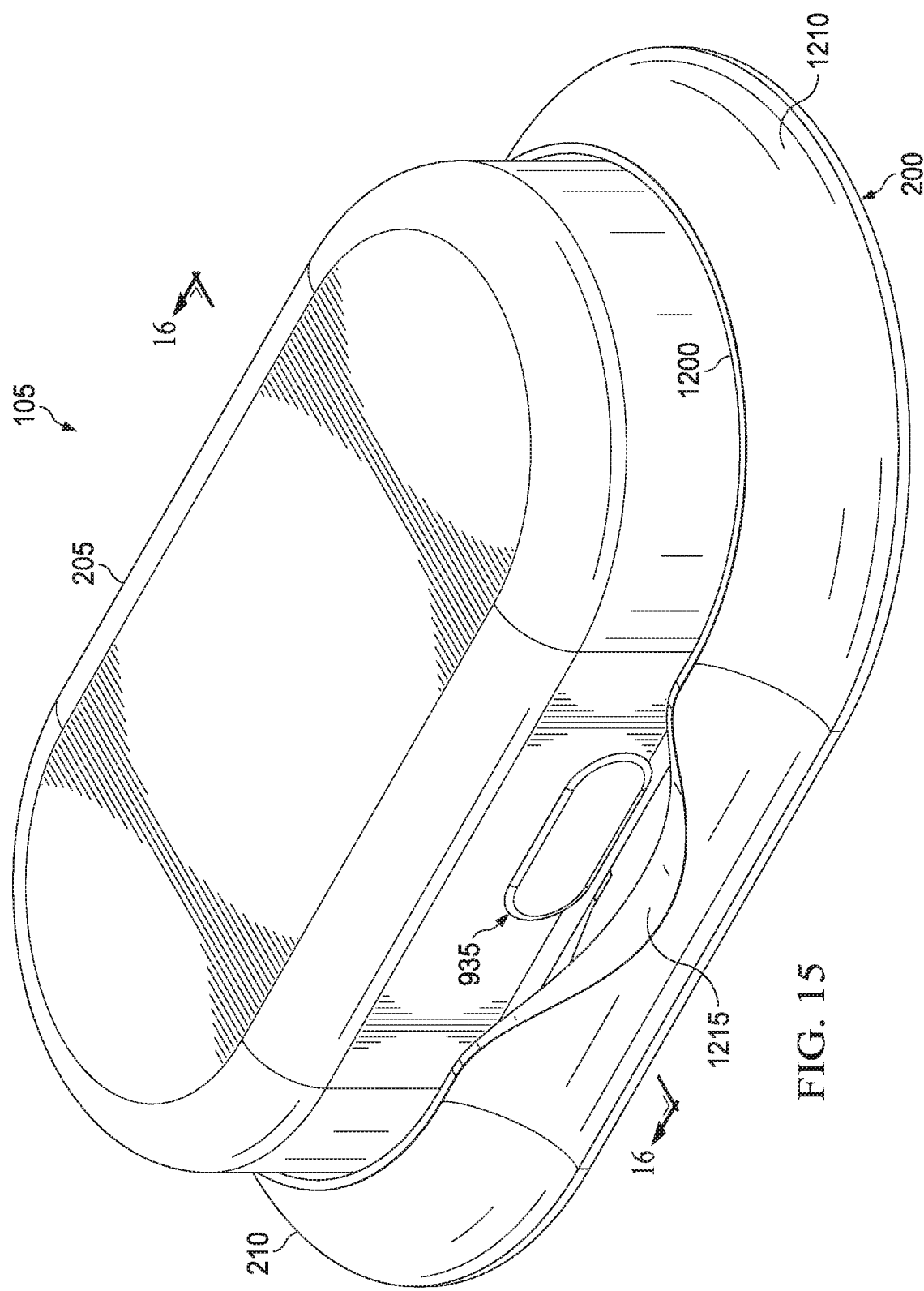
FIG. 15 is an isometric view of another example of a negative-pressure source that may be associated with some embodiments of the therapy system of FIG. 1.

FIG. 15 is an isometric view of a negative-pressure source 105 that may be associated with some embodiments of the therapy system 100. As shown in FIG. 15, the pump actuator 205 may include the mating element 935. The mating element 935 may be centrally located within the lower portion 1215 of the wall 1200 of the chamber assembly 210 when the pump actuator 205 is coupled to the pump 200. The lower portion 1215 may allow for access to the mating element 935 by a user. Additionally, the wall 1200 may be dimensioned to permit the pump actuator 205 to reside inside the perimeter of the wall 1200 when the pump actuator 205 is coupled to the pump 200. The wall 1200 may cover at least a portion of the sides of the pump actuator 205. Accordingly, the wall 1200 may reduce or prevent undercut. The wall 1200 may prevent clothing or some other object from sliding between the pump 200 and the pump actuator 205 and getting caught or pulling the pump actuator 205 off of the pump 200. The curved or filleted outer side 1210 of the wall 1200 may further cause clothing or some other object to slide over the pump actuator 205. Additionally, the wall 1200 may reduce the obviousness of the pump actuator 205 under clothing.

Figure 16:
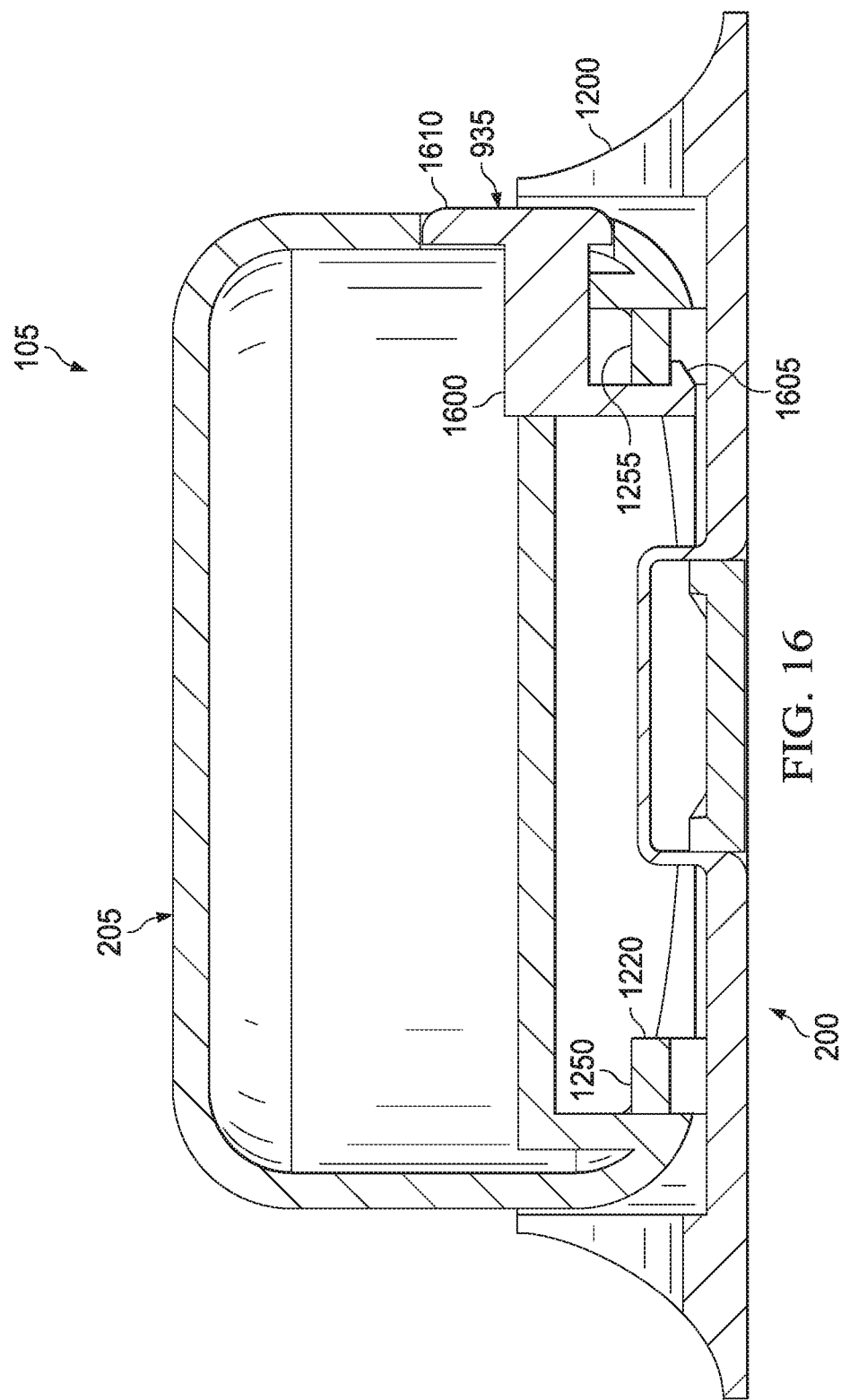
FIG. 16 is a section view of the negative-pressure source shown in FIG. 15.

FIG. 16 is a section view of the negative-pressure source 105 shown in FIG. 15 taken along line 16-16. As shown in FIG. 16, the mating element 935 of the pump actuator 205 may further include a latch 1600 having a tooth 1605 that may be configured to latch onto the first bridge 1250 or the second bridge 1255 to releasably couple the pump actuator 205 to the pump 200. The latch 1600 may be biased by a biasing element (not shown) in the latched position. The pump actuator 205 may be placed on the pump 200 within the wall 1200 and pushed down until the tooth 1605 latches or snaps onto the first bridge 1250 or the second bridge 1255. The mating element 935 may further include a button 1610 coupled to the latch 1600. The button 1610 may be depressed by a user to release the latch 1600 from the first bridge 1250 or the second bridge 1255. In some embodiments, for example, the pump actuator 205 may include two latches 1600, wherein each latch 1600 latches onto one of the first bridge 1250 or the second bridge 1255. The latch 1600 thus serves to releasably couple the pump actuator 205 to the pump 200. The frame 1220 may serve to properly locate the pump actuator 205 on the pump 200. In some embodiments, the frame 1220 may only have one bridge and the pump actuator 205 may only have one latch 1600 to ensure that the pump actuator 205 can only be coupled to the pump 200 in one way. This may ensure that the pump actuator 205 is properly coupled to the pump 200 so that the pump actuator 205 can actuate the pump 200.

FIG. 17 is a section view of another example of the pump 200 that may be associated with some embodiments of the negative-pressure source 105. As shown in FIG. 17, in some embodiments, the biasing element 1265 may comprise a flat tension spring located in the pump chamber 300 of the chamber assembly 210.

FIG. 18 is a section view of another example of the pump 200 that may be associated with some embodiments of the negative-pressure source 105. As shown in FIG. 18, in some embodiments, the biasing element 1265 may comprise a resilient member, such as an open-cell foam wedge that can be compressed and then expands to bias the chamber wall 215 upward.

The biasing elements 1265 described may reduce energy consumption by the pump actuator 205. For example, drain on the battery 415 may be reduced and the size of the motor 265 may be reduced. In some embodiments, a biasing element may be used to compress the pump 200 and a pump actuator may be used to expand the pump 200.

In various embodiments, fluid pumped by the pump 200 may not pass through the pump actuator 205. Accordingly, where the pump 200 is used to supply negative-pressure to a tissue interface, fluid removed from the tissue interface may not pass through the pump actuator 205.

Figure 19:
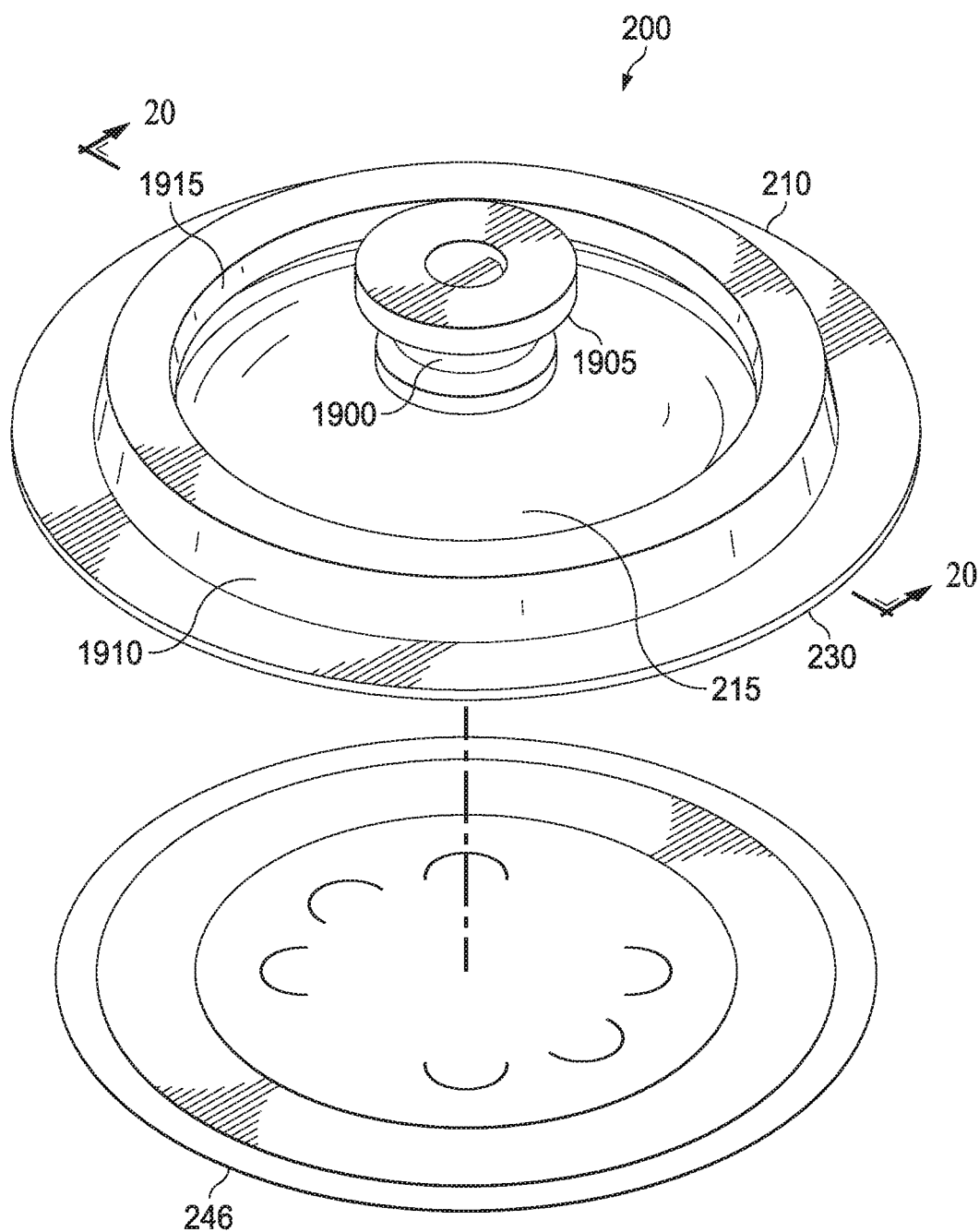
FIG. 19 is an exploded view of another example of a pump that may be associated with some embodiments of the negative-pressure source.

FIG. 19 is an exploded view of another example of the pump 200 that may be associated with some embodiments of the negative-pressure source 105. As shown in FIG. 19, the pump 200 may be a diaphragm pump. The chamber assembly 210 may comprise the chamber wall 215, a boss 1900, an inner attachment lip 1905, a rim 1910, an outer attachment lip 1915, and a base 230.

Figure 20:
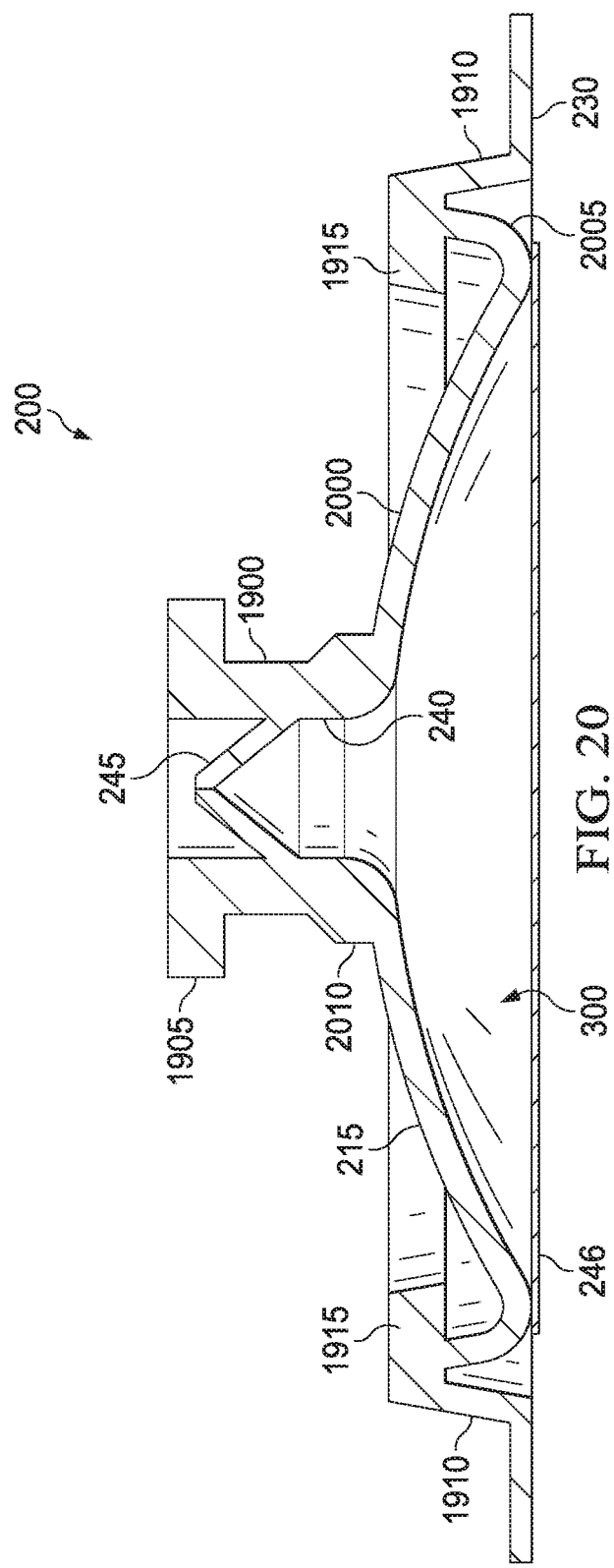
FIG. 20 is a section view of the pump shown in FIG. 19.

FIG. 20 is a section view of the pump 200 shown in FIG. 19 taken along line 20-20. In the example of FIG. 20, the chamber wall 215 of the chamber assembly 210 defines the pump chamber 300. The pump chamber 300 may be fluidly coupled to the intake valve 246. As shown in FIG. 20, the chamber wall 215 may be generally hemispherical and includes a first portion 2000, which may have a dome shape, and a second portion 2005, which may have a U-shape, extending around the periphery of the chamber wall 215.

The boss 1900 may be cylindrical and may extend away from the center of the first portion 2000. The boss 1900 may include a shoulder 2010 that may extend radially around the boss 1900 where the boss 1900 meets the dome-shaped portion 2000 of the chamber wall 215. The shoulder 2010 may provide structural support to the boss 1900. Extending through the boss 1900 may be the exhaust duct 240. The exhaust valve 245 may be located in the exhaust duct 240. The exhaust valve 245 may only permit one-way fluid flow out of the pump chamber 300. In some embodiments, for example, the exhaust valve 245 may be a duckbill valve. The chamber assembly 210 further includes the inner attachment lip 1905 which may extend radially outward from the top of the boss 1900. Additionally, the rim 1910 of the chamber assembly 210 may extend around the periphery of the chamber wall 215. In some embodiments, the outer attachment lip 1915 may extend radially inward from the top of the rim 1910. As shown in FIG. 20, the second portion 2005 of the chamber wall 215 may be coupled to the bottom side of the outer attachment lip 1915. The base 230 may extend radially outward from the bottom of the rim 1910.

In some embodiments, at least the chamber wall 215 may be formed of a resilient material. A force may act upon the chamber wall 215 to push the chamber wall 215 toward the base 230, thereby compressing or reducing the volume of the pump chamber 300. In other embodiments, the entire chamber assembly 210 may be formed of a resilient material. For example, the chamber assembly 210 may be molded from a rubber material. In various embodiments, the chamber wall 215, the boss 1900, the inner attachment lip 1905, the rim 1910, the outer attachment lip 1915, and the base 230 may be integrally formed.

Figure 21:
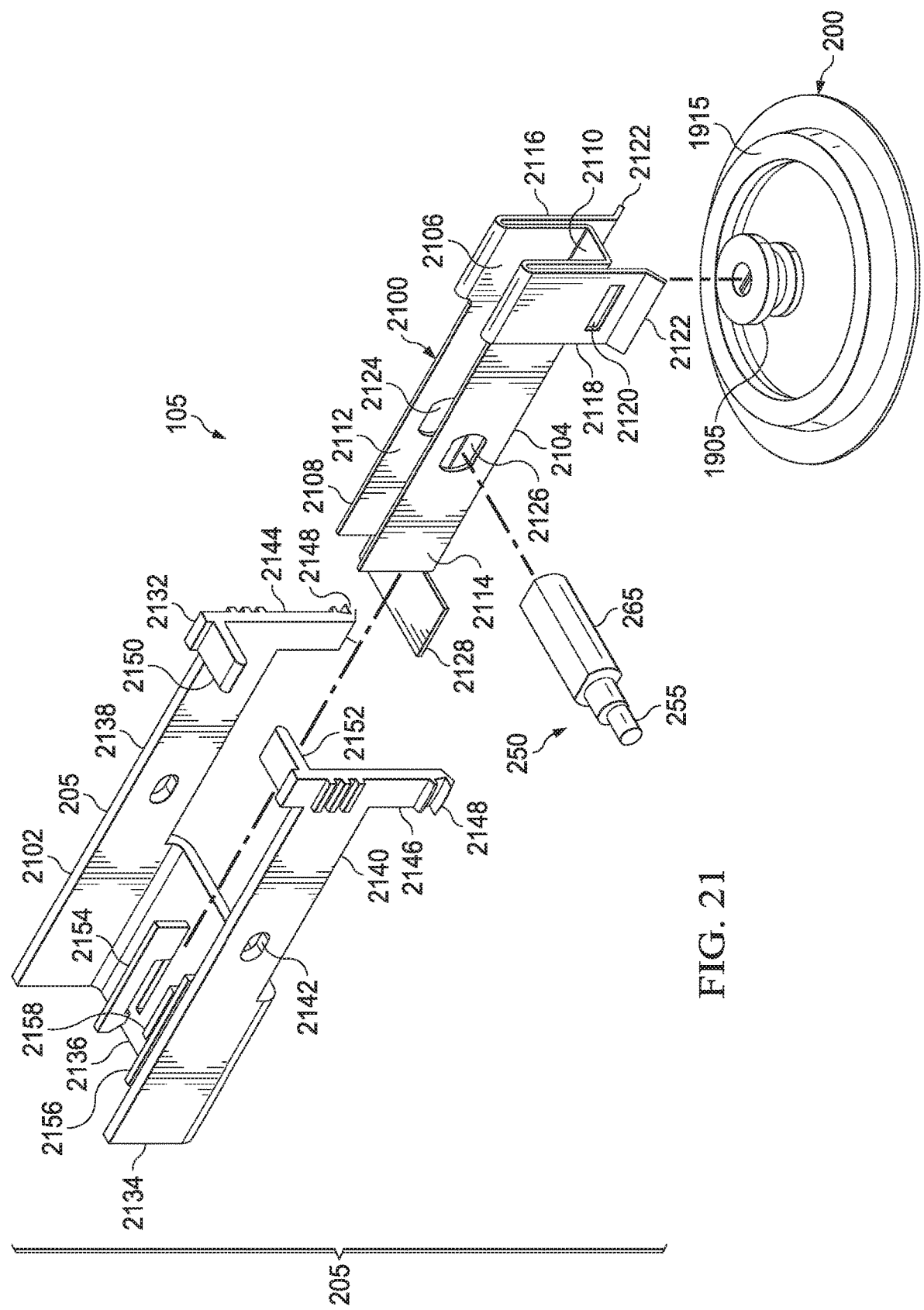
FIG. 21 is an exploded view of another example of a negative-pressure source that may be associated with some embodiments of the therapy system of FIG. 1.

FIG. 21 is an exploded view of another example of a negative-pressure source 105 that may be associated with some embodiments of the therapy system 100. In the example embodiment of FIG. 21, the pump actuator 205 may generally include an actuator arm 2100, a frame 2102, and a motor assembly 250 having a motor 265 and a cam 255.

The actuator arm 2100 comprises a body 2104 having a first end 2106 and a second end 2108. The body 2104 may be U-shaped. The body 2104 includes a base 2110 and a first leg 2112 and a second leg 2114 extending away from the base 2110. The base 2110, the first leg 2112, and the second leg 2114 may extend from the first end 2106 to the second end 2108 of the body 2104. The actuator arm 2100 may further comprise a first wing 2116 and a second wing 2118 at the first end 2106 of the body 2104. The first wing 2116 may extend downward from the top of the first leg 2112. The second wing 2118 may extend downward from the top of the second leg 2114. Each of the first wing 2116 and the second wing 2118 may include a slot 2120 that may be configured to accept and latch onto the inner attachment lip 1905 of the pump 200. In some embodiments, the slots 2120 may be located on the first wing 2116 and the second wing 2118 so that the top of the slots 2120 are in the same plane as the bottom of the base 2110. In some embodiments, each of the first wing 2116 and the second wing 2118 may further include a flared end 2122 that flares outward away from the base 2110 of the body 2104. The actuator arm 2100 may be configured to couple to the pump 200. The actuator arm 2100 may further include a first hole 2124 and a second hole 2126 in the first leg 2112 and the second leg 2114, respectively, of the body 2104. The first hole 2124 and the second hole 2126 are configured to receive the motor 265 of the motor assembly 250. Additionally, the actuator arm 2100 further includes a coupling member 2128 extending from the second end 2108 of the body 2104. The coupling member 2128 may be configured to couple the actuator arm 2100 to the frame 2102. In some embodiments, for example, the coupling member 2128 may comprise a plate extending parallel to the base of the body 2104. In some embodiments, the plate may be rectangular and may be wider than the base 2110.

The frame 2102 of the pump actuator 205 may be configured to receive the actuator arm 2100 such that the actuator arm 2100 may rotate with respect to the frame 2102. The frame 2102 may include a first end 2132 and a second end 2134. The frame 2102 may further include a base 2136 at the second end 2134. The base 2136 may be U-shaped. Extending from the base 2136 toward the first end 2132 may be a first leg 2138 and a second leg 2140. The frame 2102 may further include a cam slot 2142 in the second leg 2140, which may be configured to receive the cam 255 of the motor assembly 250. The cam 255 may be engaged with the actuator arm 2100 via the cam slot 2142. The first leg 2138 and the second leg 2140 may terminate at the first end 2132. The frame 2102 may further include a first attachment arm 2144 and a second attachment arm 2146. The first attachment arm 2144 may be on the first leg 2138 at the first end 2132 of the frame 2102. The second attachment arm 2146 may be on the second leg 2140 at the first end 2132 of the frame 2102. At least a portion of each of the first attachment arm 2144 and the second attachment arm 2146 may extend downward. As shown, for example, the first attachment arm 2144 and the second attachment arm 2146 may extend perpendicularly downward from the first leg 2138 and the second leg 2140, respectively. The bottom of each of the first attachment arm 2144 and the second attachment arm 2146 may include one or more teeth 2148 configured to cooperate with the outer attachment lip 1915 of the pump 200 to couple the frame 2102 to the pump 200. Additionally, the top of each of the first attachment arm 2144 and the second attachment arm 2146 may include a first guide member 2150 and a second guide member 2152, respectively, extending inwardly therefrom. As shown, for example, the first guide member 2150 and the second guide member 2152 may extend perpendicularly inward from the first attachment arm 2144 and the second attachment arm 2146. As further shown in FIG. 21, in some embodiments, the top of each of the first attachment arm 2144 and the second attachment arm 2146 may extend above the first leg 2138 and the second leg 2140, respectively.

The base 2136 of the frame 2102 may further include a first retention member 2154 and a second retention member 2156. The first retention member 2154 and the second retention member 2156 may be, for example, clip arms, which may be configured to retain the coupling member 2128 of the actuator arm 2100. The base 2136 may further include one or more standoffs 2158 proximate the first retention member 2154 and the second retention member 2156. The standoffs 2158 may be configured to keep the coupling member 2128 above the base 2136 of the frame 2102.

The motor 265 may be an electric motor that may be electrically coupled with and powered by a source of electrical energy. In some embodiments, for example, the motor may be a pager motor. For example, pump actuator 205 may include a battery (not shown) for supplying electrical energy to the motor 265. The pump actuator 205 may further include a printed circuit board (not shown) which may be electrically coupled with the battery and the motor 265. The printed circuit board may include various electrical elements and circuitry to control the operation of the motor 265. The pump actuator 205 may further include a switch (not shown) for turning the motor 265 ON and OFF.

Figure 22:
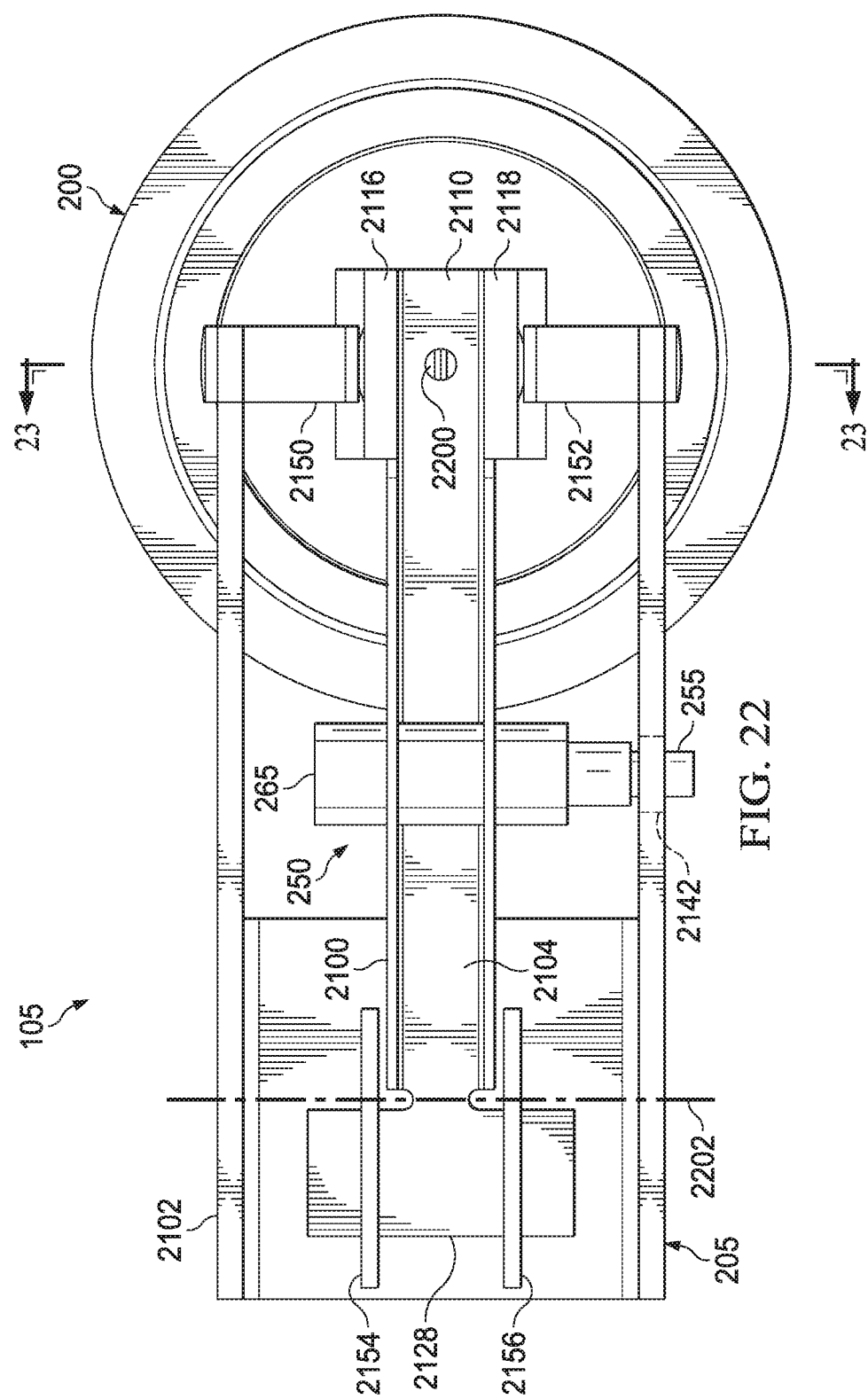
FIG. 22 is a top view of the assembled negative-pressure source of FIG. 21.

FIG. 22 is a top view of the assembled negative-pressure source 105 of FIG. 21. As shown in FIG. 22, the actuator arm 2100 may further include a passageway 2200 through the base 2110. When the pump actuator 205 is assembled, the actuator arm 2100 may be rotatably coupled to the frame 2102 by coupling member 2128. The coupling member 2128 may be fixed to the frame 2102 by the first retention member 2154 and the second retention member 2156. The body 2104 of the actuator arm 2100 may be able to flex or rotate about a pivot axis 2202. Additionally, the first wing 2116 and the second wing 2118 of the actuator arm 2100 may be received in the frame 2102 between the first guide member 2150 and the second guide member 2152. The motor 265 may be rotatably fixed with respect to the actuator arm 2100 so that the motor 265 does not rotate with respect to the actuator arm 2100. Additionally, with the motor 265 fixed to the actuator arm 2100, the cam 255 of the motor assembly 250 may be received in the cam slot 2142 of the frame 2102.

Figure 23:
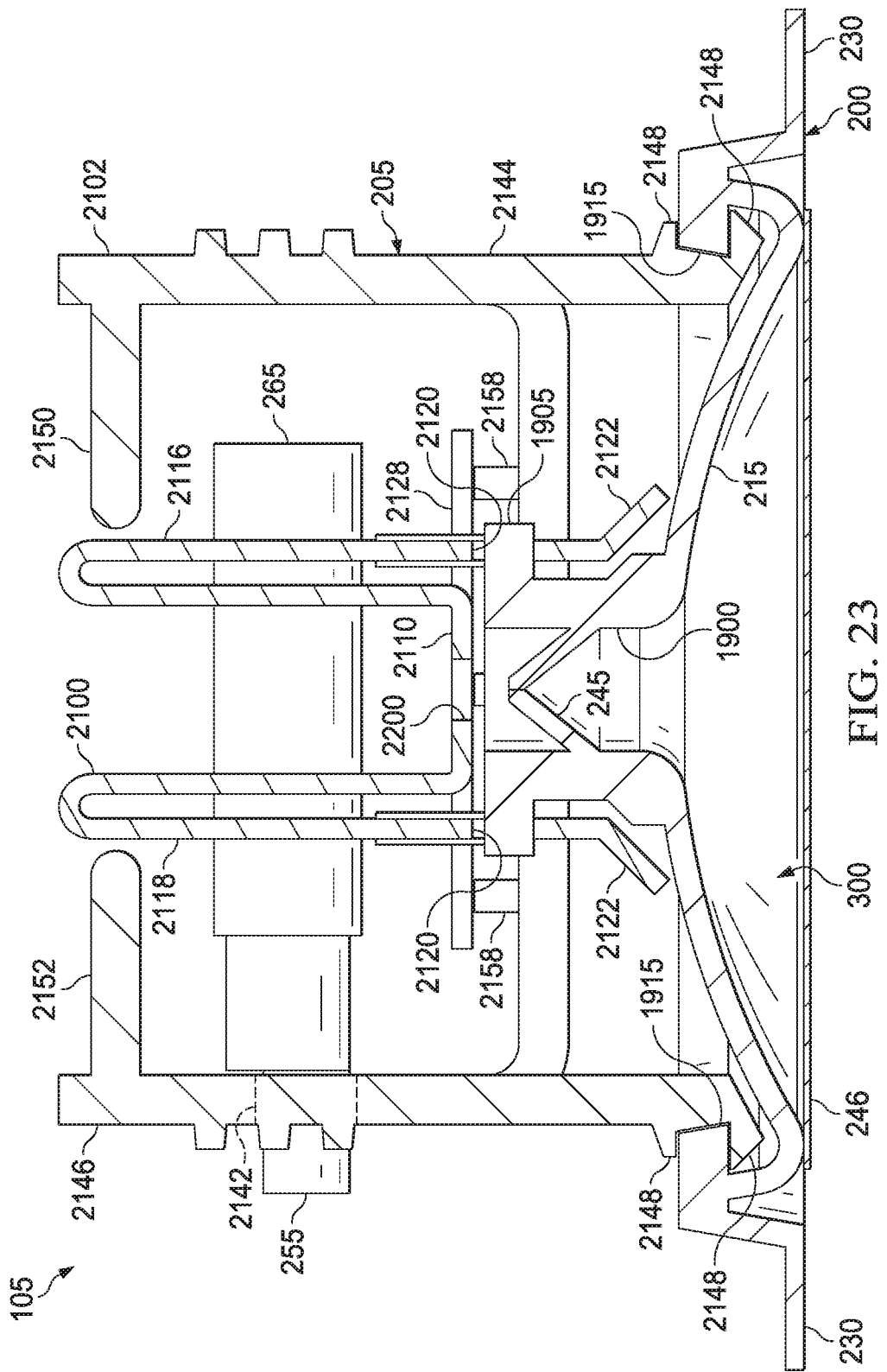
FIG. 23 is a section view of the negative-pressure source shown in FIG. 22.

FIG. 23 is a section view of the negative-pressure source 105 shown in FIG. 22 taken along line 23-23. The pump actuator 205 may be coupled to the pump 200 by the actuator arm 2100 and the frame 2102. Specifically, the actuator arm 2100 may be coupled to the boss 1900 of the pump 200 by pressing the flared ends 2122 of the first wing 2116 and the second wing 2118 down on the inner attachment lip 1905 of the pump 200, causing the first wing 2116 and the second wing 2118 to spread outward. The first wing 2116 and the second wing 2118 may then slide down inner attachment lip 1905 until the inner attachment lip 1905 snaps into the slots 2120 in the first wing 2116 and the second wing 2118. The first wing 2116 and the second wing 2118 may then spring back and retain the inner attachment lip 1905 within the slots 2120. Additionally, the frame 2102 may be coupled to pump 200 by engaging the teeth 2148 of the first attachment arm 2144 and the second attachment arm 2146 onto the outer attachment lip 1915. For example, the first attachment arm 2144 and the second attachment arm 2146 may be pressed inward toward one another and then may be pressed downward until the teeth 2148 engagingly align with the outer attachment lip 1915. Once aligned, the pressing force may be removed and the first attachment arm 2144 and the second attachment arm 2146 may spring outward away from one another and engage with the outer attachment lip 1915.

With the pump actuator 205 coupled to the pump 200 and when the motor 265 is turned on, the motor 265 rotates the cam 255 within the cam slot 2142 of the frame 2102. The rotational motion of the cam 255 within the cam slot 2142 results in a translation of the motor 265 in a generally up-and-down motion. Because the motor 265 is coupled to the actuator arm 2100, the translation of the motor 265 results in a translation of the actuator arm 2100 in a generally up-and-down motion. The actuator arm 2100 moves in relation to the frame 2102. The motion of the actuator arm 2100 cyclically pushes the chamber wall 215 toward the base 230, compressing the pump chamber 300, and then pulls the chamber wall 215 away from the base 230, expanding the pump chamber 300. On the downward stroke, fluid is evacuated from the pump chamber 300, through the exhaust valve 245, and through the passageway 2200. On the upward stroke, fluid is drawn into the pump chamber 300 through the intake valve 246 and the pump chamber 300 is expanded. This cyclic compression and expansion of the pump chamber 300 creates a negative pressure in the pump chamber 300, wherein this negative pressure may be supplied to a tissue interface to decrease the pressure in the tissue interface.

Figure 24:
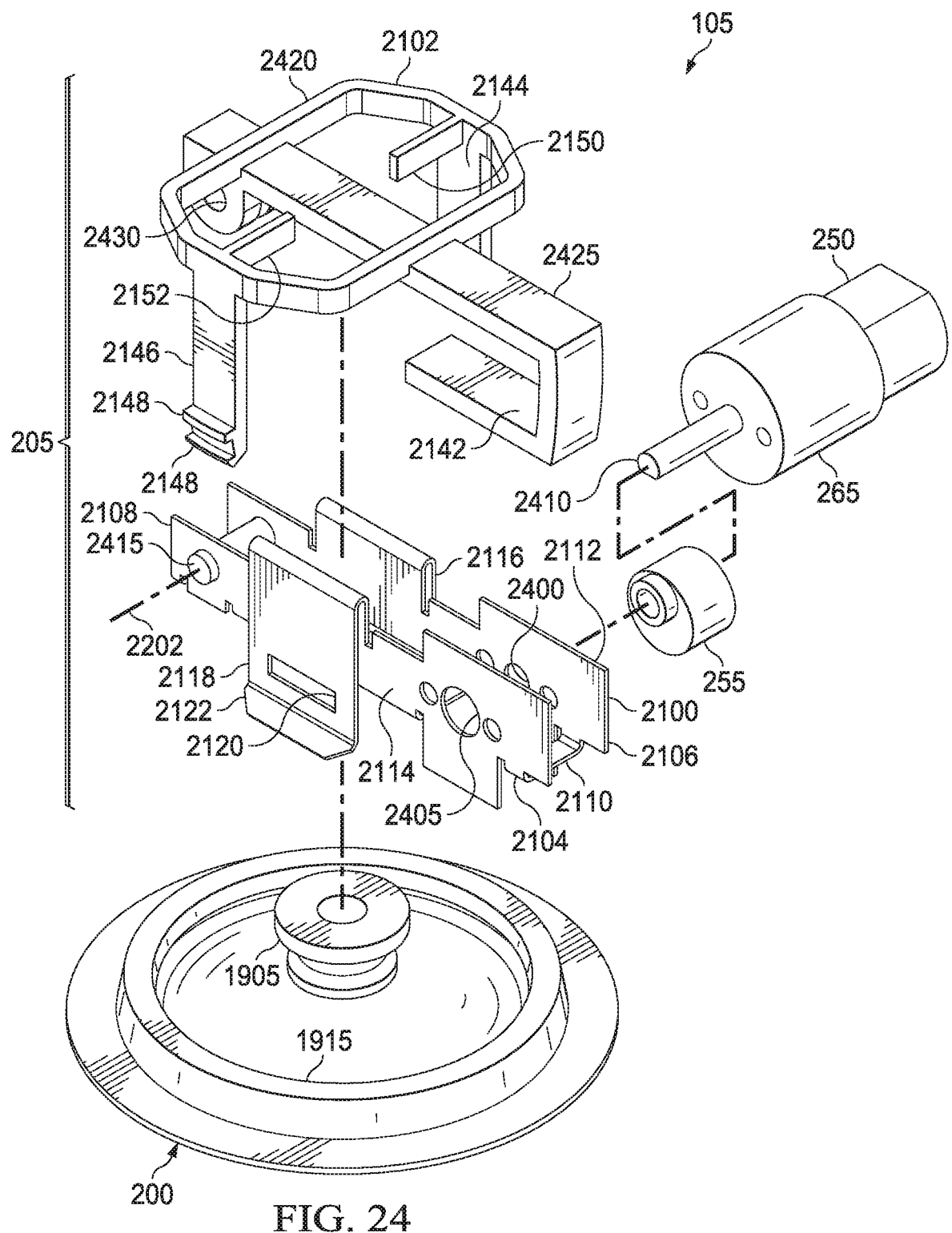
FIG. 24 is an exploded view of another example of a negative-pressure source that may be associated with some embodiments of the therapy system of FIG. 1.

FIG. 24 is an exploded view of another example of a negative-pressure source 105 that may be associated with some example embodiments of the therapy system 100. In the example embodiment of FIG. 24, the pump actuator 205 may generally include the actuator arm 2100, the frame 2102, and the motor assembly 250 having the motor 265 and the cam 255.

The actuator arm 2100 may further comprise the first wing 2116 and the second wing 2118 between the first end 2106 and the second end 2108 of the body 2104. As shown in FIG. 24, the first wing 2116 and the second wing 2118 may be located midway between the first end 2106 and the distal end 2108. Each of the first wing 2116 and the second wing 2118 may include the slot 2120 that may be configured to accept and latch onto the inner attachment lip 1905 of the pump 200. In some embodiments, each of the first wing 2116 and the second wing 2118 may further include the flared end 2122. The actuator arm 2100 may further include a first driveshaft hole 2400 and a second driveshaft hole 2405 extending through the first leg 2112 and the second leg 2114, respectively, proximate the first end 2106. The first driveshaft hole 2400 and the second driveshaft hole 2405 may be configured to receive the driveshaft 2410 of the motor 265. Additionally, the cam 255 may be configured to be located between the first leg 2112 and the second leg 2114 proximate the first driveshaft hole 2400 and the second driveshaft hole 2405. The driveshaft 2410 may extend through the first driveshaft hole 2400, the cam 255, and the second driveshaft hole 2405. Additionally, the actuator arm 2100 of FIG. 24 further includes a pivot pin 2415 extending between the first leg 2112 and the second leg 2114 proximate the second end 2108 of the body 2104. The actuator arm 2100 may be configured to rotate about the pivot axis 2202 extending through pivot pin 2415.

The frame 2102 of the pump actuator 205 may be configured to receive the actuator arm 2100 such that the actuator arm 2100 may rotate with respect to the frame 2102. In the example of FIG. 24, the frame 2102 may include an upper body 2420. As shown, for example, the upper body 2420 may have an elongated octagonal shape. However, the upper body 2420 may have other shapes, such as for example, circular, ovular, rectangular, square, hexagonal, pentagonal, and rectilinear. The frame 2102 may further include a cam engagement member 2425 coupled to the upper body 2420. In the example of FIG. 24, the cam slot 2142 is disposed at a first end of the cam engagement member 2425, and a pivot hole 2430 may be disposed at a second end, opposite the first end. The pivot pin 2415 may be received in the pivot hole 2430. In some embodiments, the pivot pin 2415 may be rotatably fixed in the pivot hole 2430. In some embodiments, the pivot pin 2415 may rotate with respect to the pivot hole 2430. Additionally, the cam 255 may be received in the cam slot 2142. The frame 2102 may further include the first attachment arm 2144 and the second attachment arm 2146 extending downward from opposite sides of the upper body 2420. The bottom of each of the first attachment arm 2144 and the second attachment arm 2146 may include one or more teeth 2148 configured to cooperate with the outer attachment lip 1915 of the pump 200 to couple the frame 2102 to the pump 200. Additionally, the frame 2102 may further include the first guide member 2150 and the second guide member 2152, extending inwardly from the upper body 2420. The first guide member 2150 and the second guide member 2152 may be located proximate the first attachment arm 2144 and the second attachment arm 2146, respectively.

Figure 25:
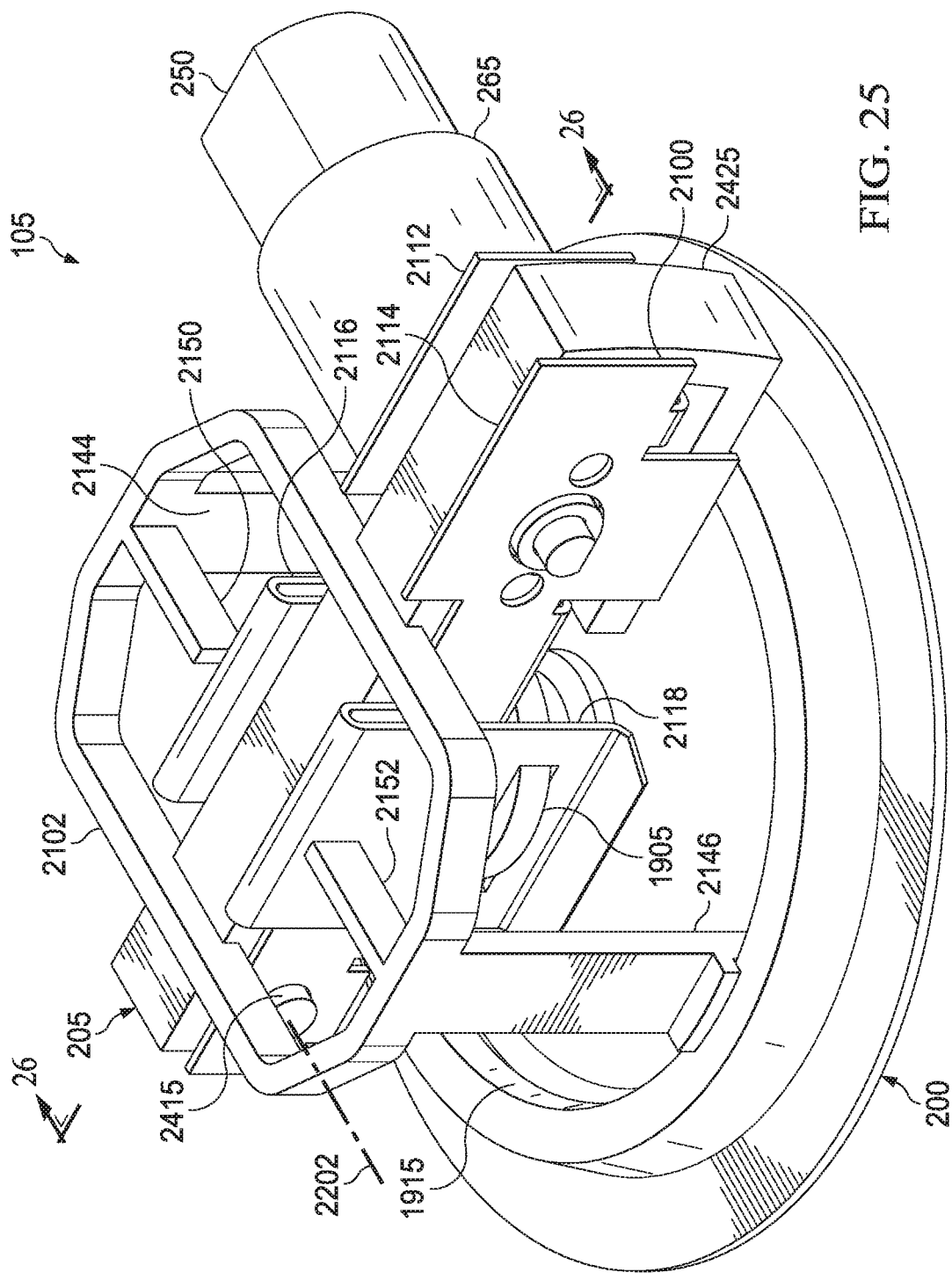
FIG. 25 is an assembled view of the negative-pressure source of FIG. 24.

FIG. 25 is an assembled view of the negative-pressure source 105 of FIG. 24. When the pump actuator 205 is assembled, the actuator arm 2100 may be rotatably coupled to the frame 2102 by the pivot pin 2415. The actuator arm 2100 may be able to rotate about the pivot axis 2202. Additionally, the first wing 2116 and the second wing 2118 of the actuator arm 2100 may be received in the frame 2102 between the first guide member 2150 and the second guide member 2152. The motor 265 may be rotatably fixed to the actuator arm 2100 so that the motor 265 does not rotate with respect to the actuator arm 2100. For example, in some embodiments, the motor 265 may be fixed to the actuator arm 2100 by one or more screws. Additionally, the first wing 2116 and the second wing 2118 of the actuator arm 2100 may be coupled to the inner attachment lip 1905 of the pump 200. The first attachment arm 2144 and the second attachment arm 2146 of the frame 2102 may be coupled to the outer attachment lip 1915 of the pump 200.

Figure 26:
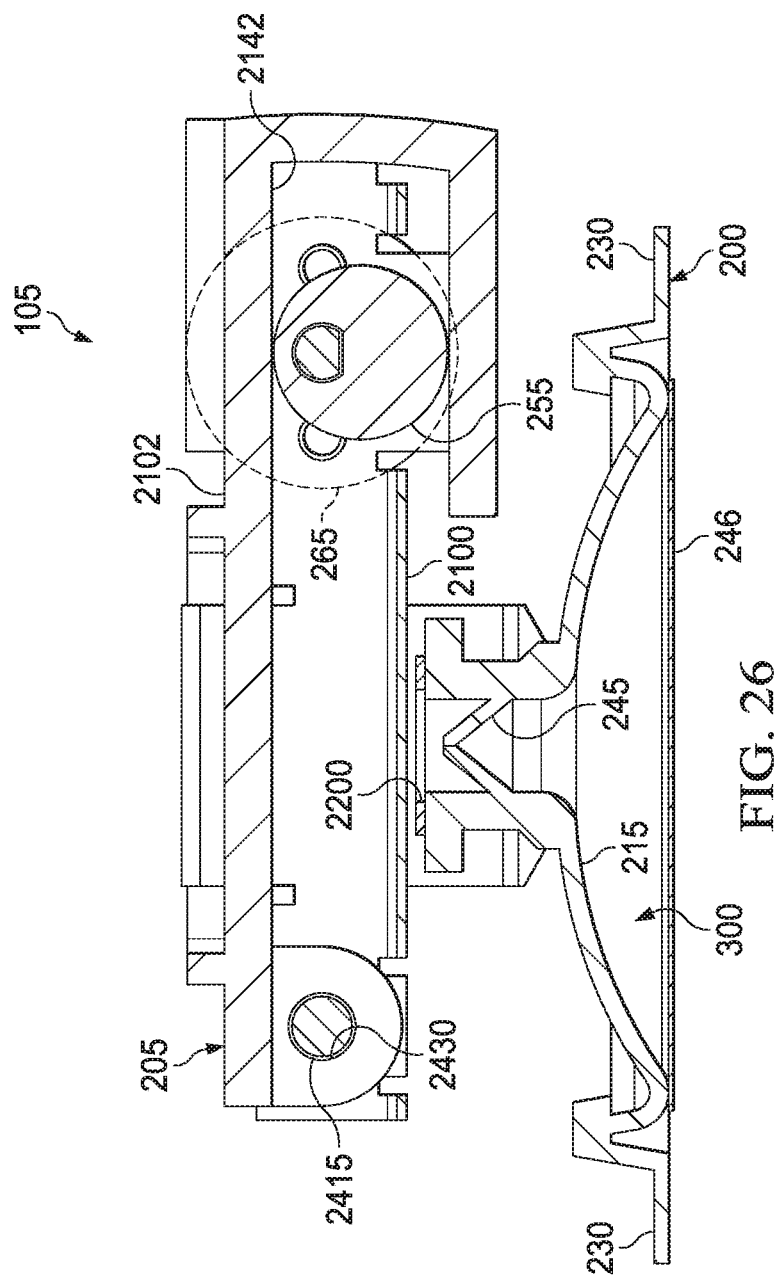
FIG. 26 is a section view of the negative-pressure source shown in FIG. 25.

FIG. 26 is a section view of the negative-pressure source 105 shown in FIG. 25 taken along line 26-26. As shown in FIG. 26, the cam 255 may be received in the cam slot 2142 of the frame 2102. Additionally, the pivot pin 2415 may be received in the pivot hole 2430 of the frame 2102. With the pump actuator 205 coupled to the pump 200 and when the motor 265 is turned on, the motor 265 rotates the cam 255 within the cam slot 2142 of the frame 2102. The rotational motion of the cam 255 within the cam slot 2142 results in a translation of the motor 265 in a generally up-and-down motion. Because the motor 265 is coupled to the actuator arm 2100, the translation of the motor 265 results in a translation of the actuator arm 2100 in a generally up-and-down motion. The actuator arm 2100 moves in relation to the frame 2102. The motion of the actuator arm 2100 cyclically pushes the chamber wall 215 toward the base 230, compressing the pump chamber 300, and then pulls the chamber wall 215 away from the base 230, expanding the pump chamber 300. On the downward stroke, fluid is evacuated from the pump chamber 300, through the exhaust valve 245, and through the passageway 2200. On the upward stroke, fluid is drawn into the pump chamber 300 through the intake valve 246 and the pump chamber 300 is expanded. This cyclic compression and expansion of the pump chamber 300 creates a negative pressure in the pump chamber 300, wherein this negative pressure may be supplied to a tissue interface to decrease the pressure in the tissue interface.

Figure 27:
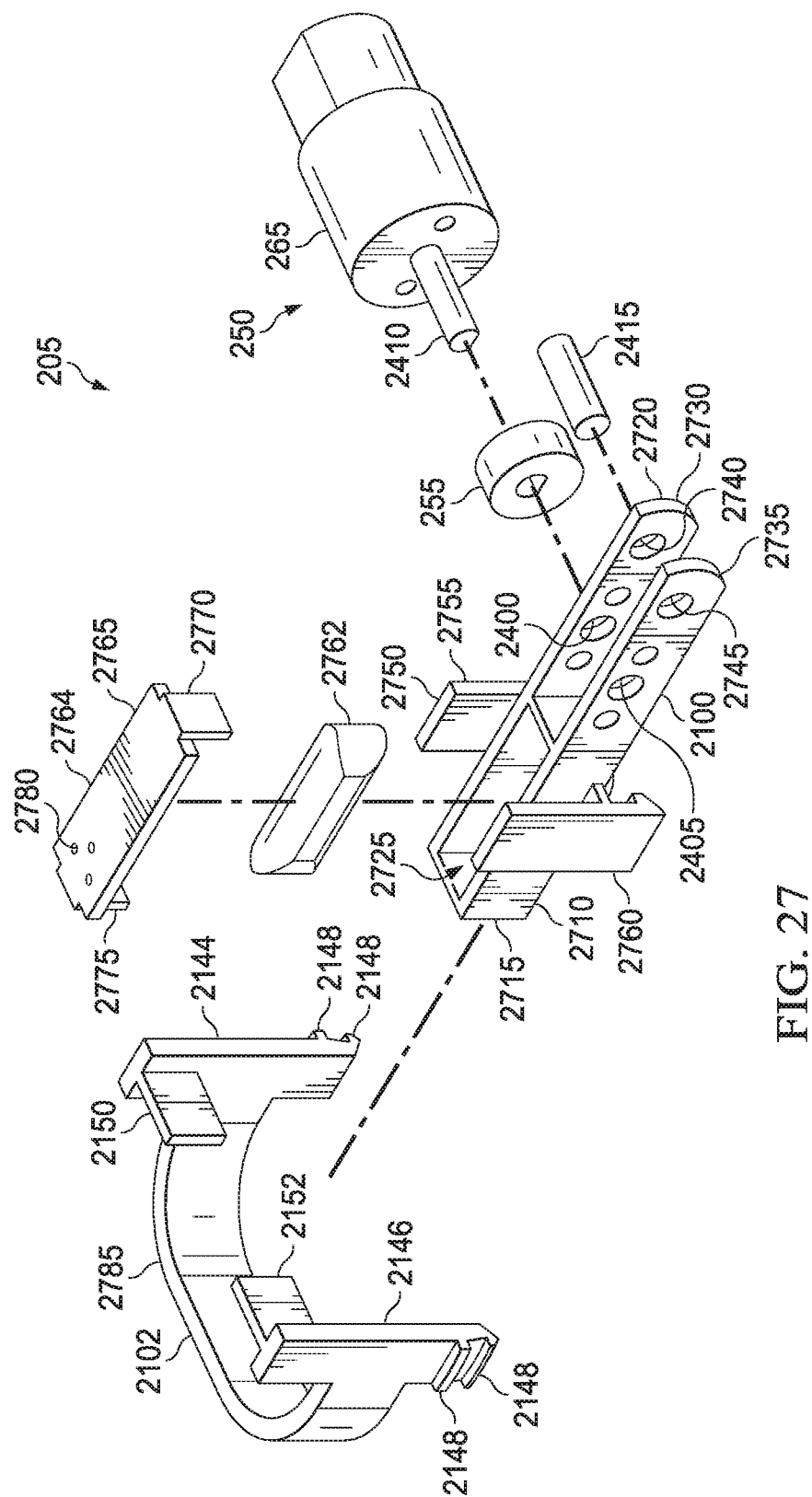
FIG. 27 is an exploded view of an example of a pump actuator that may be associated with some embodiments of the negative-pressure source.

FIG. 27 is an exploded view of the pump actuator 205 illustrating additional details of a negative-pressure source 105 that may be associated with some example embodiments of the therapy system 100.

The actuator arm 2100 comprises an elongate body 2710 having a first end 2715 and a second end 2720. The actuator arm 2100 may include a receptacle 2725 proximate the first end 2715. The actuator arm 2100 may further include a first arm 2730 and a second arm 2735 extending away from the receptacle 2725 and terminating at the second end 2720. The first arm 2730 and the second arm 2735 may be spaced apart a distance. The first arm 2730 may include a first pivot hole 2740 proximate the second end 2720. The second arm 2735 may include a second pivot hole 2745 proximate the second end 2720. The first pivot hole 2740 and the second pivot hole 2745 may be configured to receive the pivot pin 2415. The actuator arm 2100 may further include the first driveshaft hole 2400 and the second driveshaft hole 2405 extending through the first arm 2730 and the second arm 2735, respectively, between the receptacle 2725 and the second end 2720. Additionally, the actuator arm 2100 may further include a clip assembly 2750 proximate to the first end 2715. The clip assembly 2750 may comprise a first clip arm 2755 and a second clip arm 2760.

A desiccant 2762 may be received in the receptacle 2725 of the actuator arm 2100. A desiccant cover 2764 may include a cover portion 2765, a first clip arm 2770, and a second clip arm 2775. The first clip arm 2770 may extend downward from a first end of the desiccant cover 2764 and the second clip arm 2775 may extend downward from a second end of the desiccant cover 2764 opposite the first end. Additionally, one or more apertures 2780 may extend through the cover portion 2765 to provide a fluid pathway through the desiccant cover 2764. The apertures 2780 may serve as a vent. The first clip arm 2770 and the second clip arm 2775 may be configured to clip onto the actuator arm 2100 to retain the desiccant cover 2764 over the receptacle 2725, and thus retain the desiccant 2762 in the receptacle 2725. The desiccant 2762 may be configured to absorb moisture and/or odors from a tissue site.

The frame 2102 may comprise a body 2785 having two terminal ends. In some embodiments, as shown in FIG. 27, the body 2785 may be C-shaped. The frame 2102 may further include a first attachment arm 2144 at a first terminal end of the body 2785 and a second attachment arm 2146 at a second terminal end of the body 2785. The bottom of each of the first attachment arm 2144 and the second attachment arm 2146 may include one or more teeth 2148. Additionally, the top of each of the first attachment arm 2144 and the second attachment arm 2146 may include the first guide member 2150 and the second guide member 2152, respectively, extending inwardly therefrom.

Figure 28:
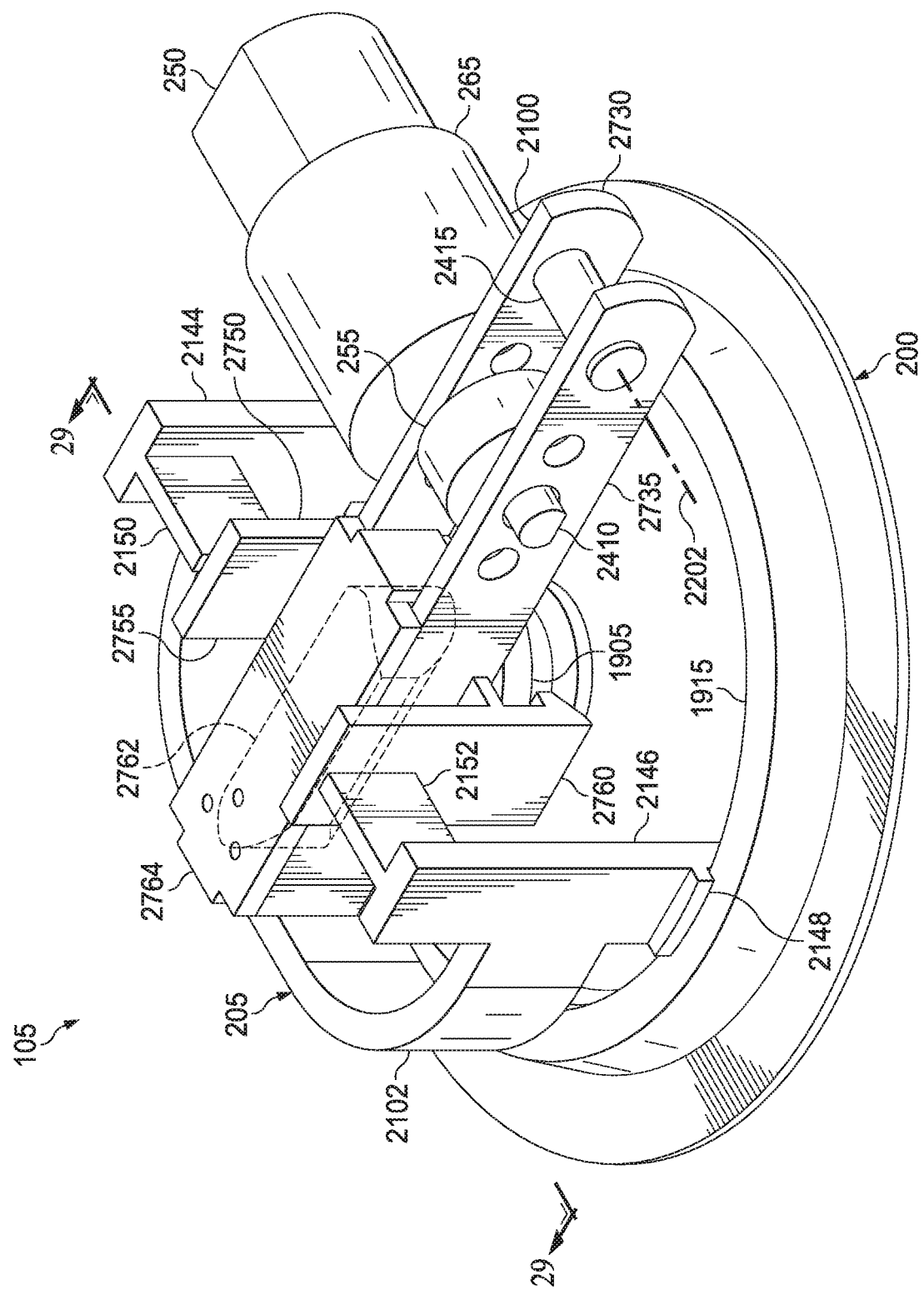
FIG. 28 is an isometric view of the pump actuator of FIG. 27 with an example of a negative-pressure source that may be associated with some embodiments of the therapy system of FIG. 1.

FIG. 28 is an isometric view of the pump actuator of FIG. 27 with an example of the pump 200 that may be associated with some embodiments of the therapy system 100. The negative-pressure source 105 may comprise the pump actuator 205 shown in FIG. 27 and the pump 200 shown in FIG. 16. As shown in FIG. 28, the frame 2102 may be coupled to the outer attachment lip 1915 by the teeth 2148. The actuator arm 2100 may be coupled to the inner attachment lip 1905 by the clip assembly 2750. Additionally, the first clip arm 2755 and the second clip arm 2760 of the clip assembly 2750 of actuator arm 2100 may be located between the first guide member 2150 and the second guide member 2152. Additionally, as shown in FIG. 28 the desiccant 2762 may be received in the receptacle 2725 and the desiccant cover 2764 may be coupled to the actuator arm 2100 to retain the desiccant 2762 in the receptacle 2725. Further, the cam 255 may be located between the first arm 2730 and the second arm 2735 of the actuator arm 2100 and the cam 255 may be coupled to the driveshaft 2410 of the motor 265. The motor 265 may be rotatably fixed with respect to the actuator arm 2100 so that the motor 265 does not rotate with respect to the actuator arm 2100. Additionally, the pivot pin 2415 may be received in the actuator arm 2100. The actuator arm 2100 may be configured to rotate about a pivot axis 2202 extending through pivot pin 2415.

Figure 29:
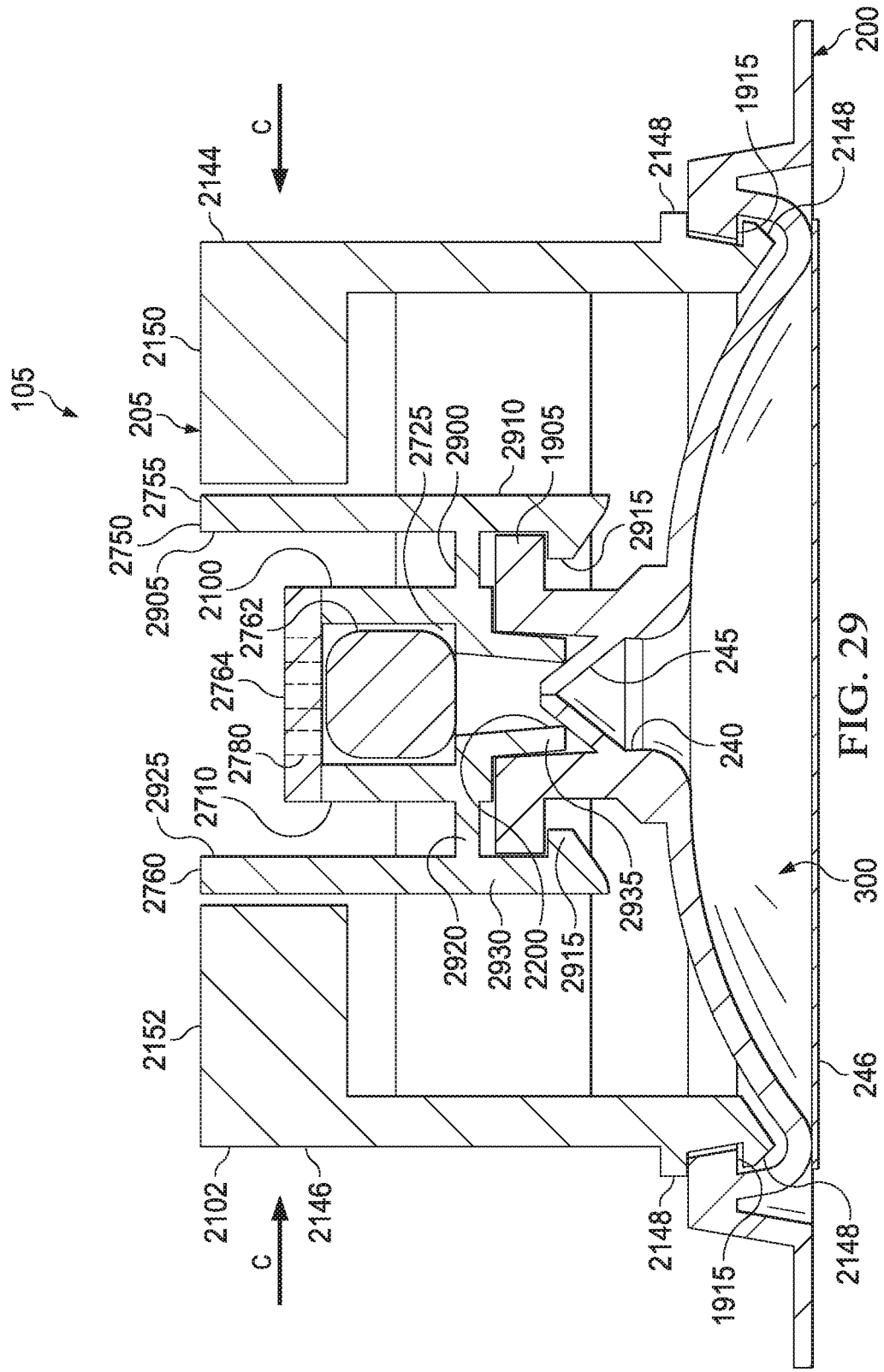
FIG. 29 is a section view of the negative-pressure source shown in FIG. 28.

FIG. 29 is a section view of the negative-pressure source 105 shown in FIG. 28 along line 29-29. As shown in FIG. 29, the first clip arm 2755 of the clip assembly 2750 may be pivotably affixed to the outside of the elongate body 2710 of the actuator arm 2100 by a first fulcrum member 2900. The first clip arm 2755 may have a first effort arm portion 2905 extending upward from the first fulcrum member 2900 and a first load arm portion 2910 extending downward from the first fulcrum member 2900. The first clip arm 2755 may further include one or more teeth 2915 extending inward that are configured to engage the inner attachment lip 1905 to couple the actuator arm 2100 to the pump 200. Additionally, the second clip arm 2760 of the clip assembly 2750 may be pivotably affixed to the outside of the elongate body 2710 of the actuator arm 2100 by a second fulcrum member 2920. The second clip arm 2760 may have a second effort arm portion 2925 extending upward from the second fulcrum member 2920 and a second load arm portion 2930 extending downward from the second fulcrum member 2920. The second clip arm 2760 may further include one or more teeth 2915 extending inward that are configured to engage the inner attachment lip 1905 to couple the actuator arm 2100 to the pump 200.

As shown in FIG. 29, the actuator arm 2100 may further include a projection 2935 extending downward from the elongate body 2710. The projection 2935 may be located below the receptacle 2725 and between the first clip arm 2755 and the second clip arm 2760. The projection 2935 may further include the passageway 2200 extending through the projection 2935. The passageway 2200 fluidly couples the receptacle 2725 with the pump chamber 300. At least a portion of the projection 2935 may extend at least partially into the exhaust duct 240. In some embodiments, the projection 2935 may provide structural stability to the exhaust duct 240. A fluid passageway may exist from the pump chamber 300, through the exhaust valve 245, through the passageway 2200, through the desiccant 2762, and through the apertures 2780 in the desiccant cover 2764. During operation of the pump actuator 205, exhaust from the pump chamber 300 passes through this fluid passageway.

As further shown in FIG. 29, the teeth 2148 on the first attachment arm 2144 and the second attachment arm 2146 of the frame 2102 are shown engaged with the outer attachment lip 1915 of the pump to couple the frame 2102 to the pump 200.

In some embodiments, the pump actuator 205 may be removed from the pump 200 by pushing the top of the first attachment arm 2144 and the second attachment arm 2146 toward one another as shown by arrows C. If the first attachment arm 2144 and the second attachment arm 2146 are pushed inward, the teeth 2148 of the first attachment arm 2144 and the second attachment arm 2146 disengage with the outer attachment lip 1915. Additionally, if the first attachment arm 2144 and the second attachment arm 2146 are pushed inward, the first guide member 2150 and the second guide member 2152 push against the first effort arm portion 2905 and the second effort arm portion 2925, respectively, pushing them inward and the first load arm portion 2910 and the second load arm portion 2930 outward. This disengages the teeth 2915 of the first clip arm 2755 and the second clip arm 2760 from the inner attachment lip 1905. The pump actuator 205 can then be lifted from the pump 200.

Figure 30:
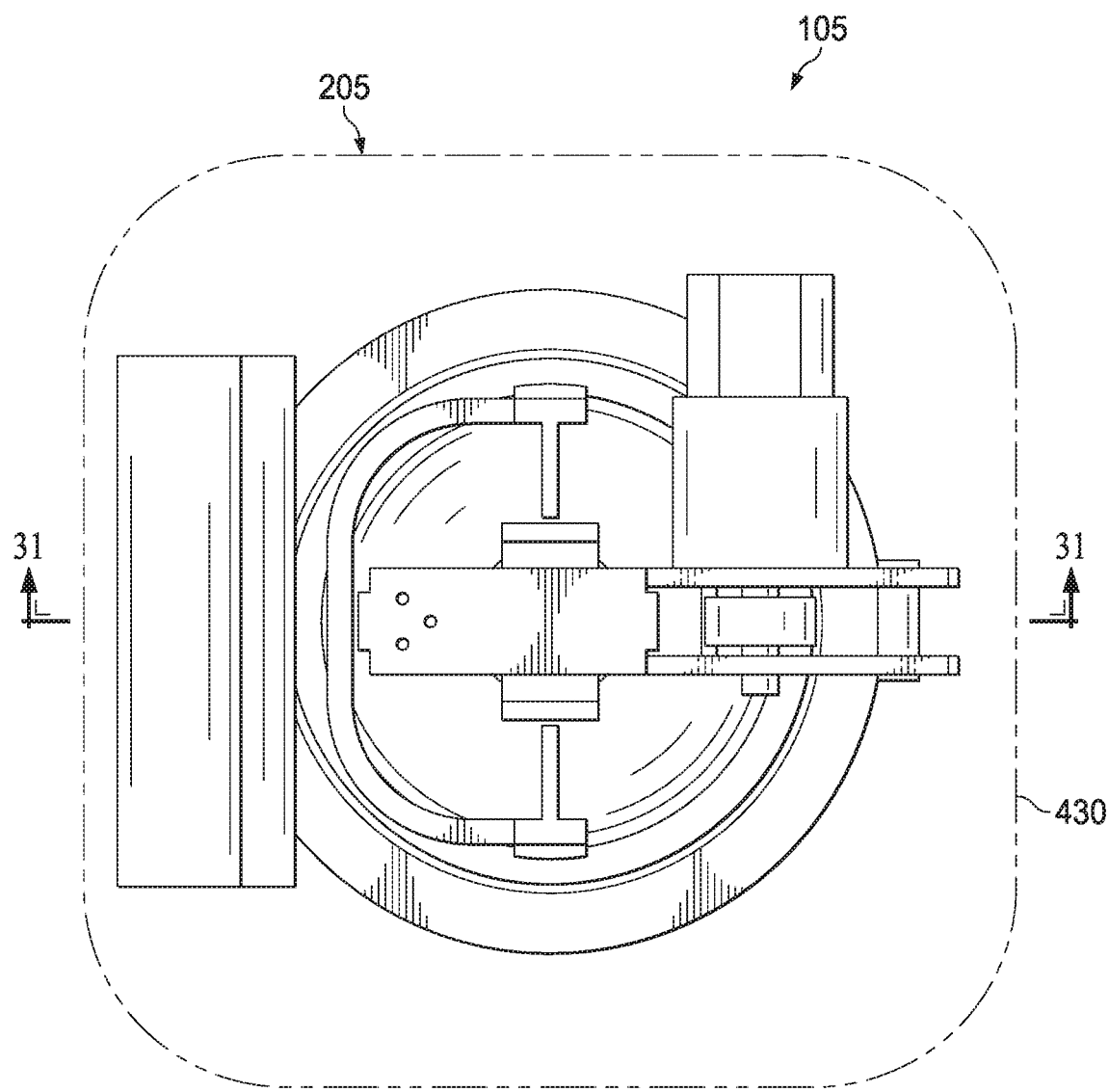
FIG. 30 is a top view of the negative-pressure source shown in FIG. 28.

FIG. 30 is a top view of the negative-pressure source 105 shown in FIG. 28 illustrating additional details that may be associated with some embodiments of the therapy system 100. FIG. 30 illustrates another example of the housing 430, which can enclose the pump actuator 205.

Figure 31:
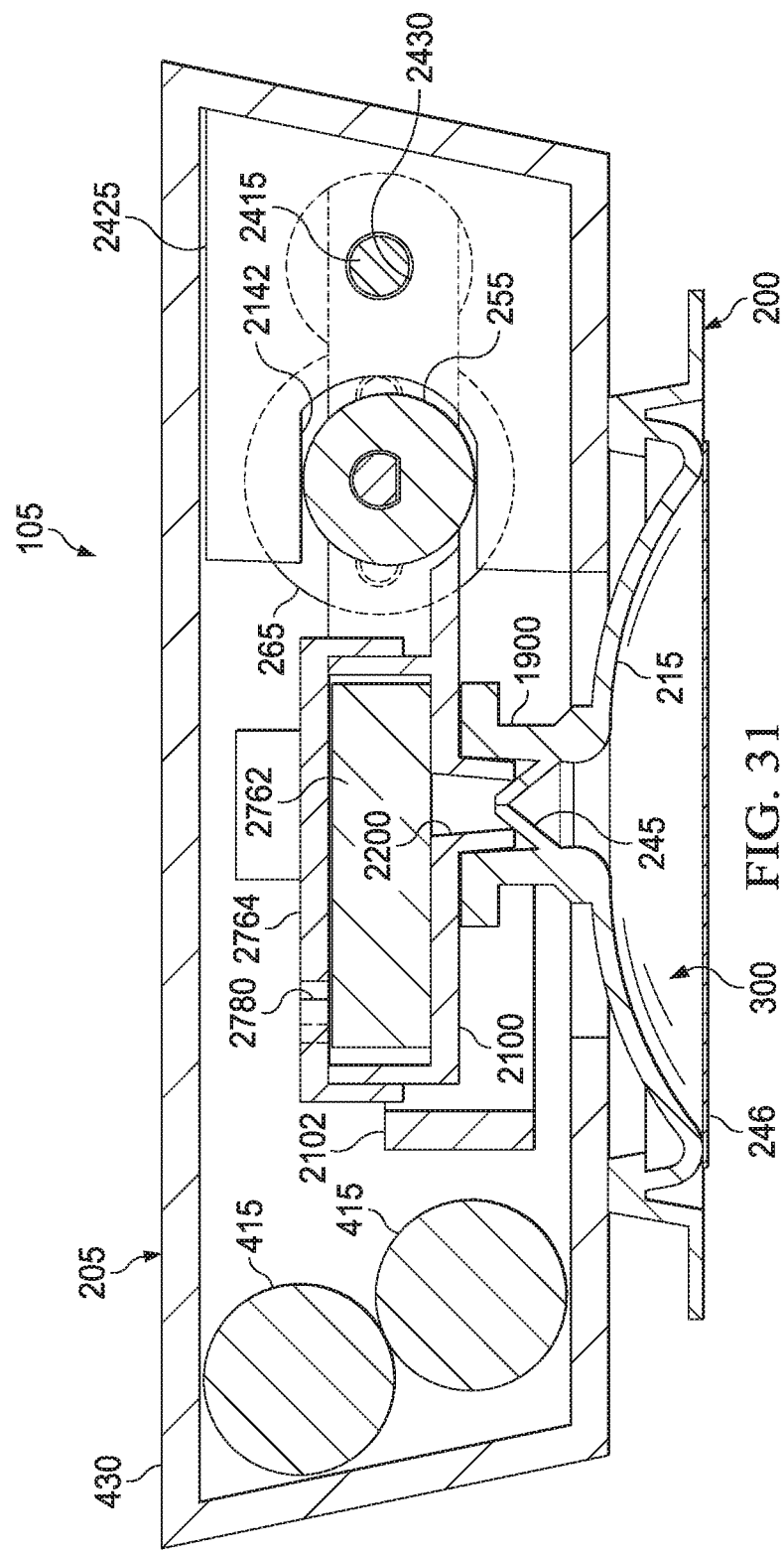
FIG. 31 is a section view of the negative-pressure source shown in FIG. 30.

FIG. 31 is a section view of the negative-pressure source 105 shown in FIG. 30 along line 31-31. As shown in FIG. 31, in some embodiments, the pump actuator 205 may further include the housing 430, which encloses the actuator arm 2100, the frame 2102, the desiccant 2762, the desiccant cover 2764, the motor 265, the cam 255, and the pivot pin 2415. Additionally, the pump actuator 205 may include a source of electrical energy, such as for example, one or more batteries 415, that are electrically coupled with and power the motor 265. The pump actuator 205 may further include a cam engagement member 2425, which may be fixed within the housing 430. The cam engagement member 2425 includes a cam slot 2142 and a pivot hole 2430. The pivot pin 2415 may be received in the pivot hole 2430. In some embodiments, the pivot pin 2415 may be rotatably fixed in the pivot hole 2430. In some embodiments, the pivot pin 2415 may rotate with respect to the pivot hole 2430. Additionally, the cam 255 may be received in the cam slot 2142.

In operation, when the motor 265 of the pump actuator 205 receives electrical power, the motor 265 rotates the cam 255 within the cam slot 2142 of the frame 2102. The rotational motion of the cam 255 within the cam slot 2142 results in a translation of the motor 265 in a generally up-and-down motion. The translation of the motor thus results in a pivoting motion of the actuator arm 2100 about the pivot axis 2202. With the actuator arm 2100 coupled to the boss 1900 of the pump 200, the pivoting motion of the actuator arm 2100 cyclically pushes the chamber wall 215 downward, compressing the pump chamber 300, and then pulls the chamber wall 215 upward, expanding the pump chamber 300. On the downward stroke, fluid is evacuated from the pump chamber 300 through the exhaust valve 245, through the passageway 2200, through the desiccant 2762, and through the apertures 2780 in the desiccant cover 2764. On the upward stroke, fluid is drawn into the pump chamber 300 through the intake valve 246 and the pump chamber 300 is expanded. This cyclic compression and expansion of the pump chamber 300 creates a negative pressure in the pump chamber 300, wherein this negative pressure may be supplied to a tissue interface to decrease the pressure in the tissue interface.

Although not illustrated in FIG. 31, in some embodiments, the pump actuator 205 may further include a printed circuit board which may be electrically coupled with the source of electrical energy and the motor 265. The printed circuit board may include various electrical elements and circuitry to control the operation of the motor 265.

Figure 32:
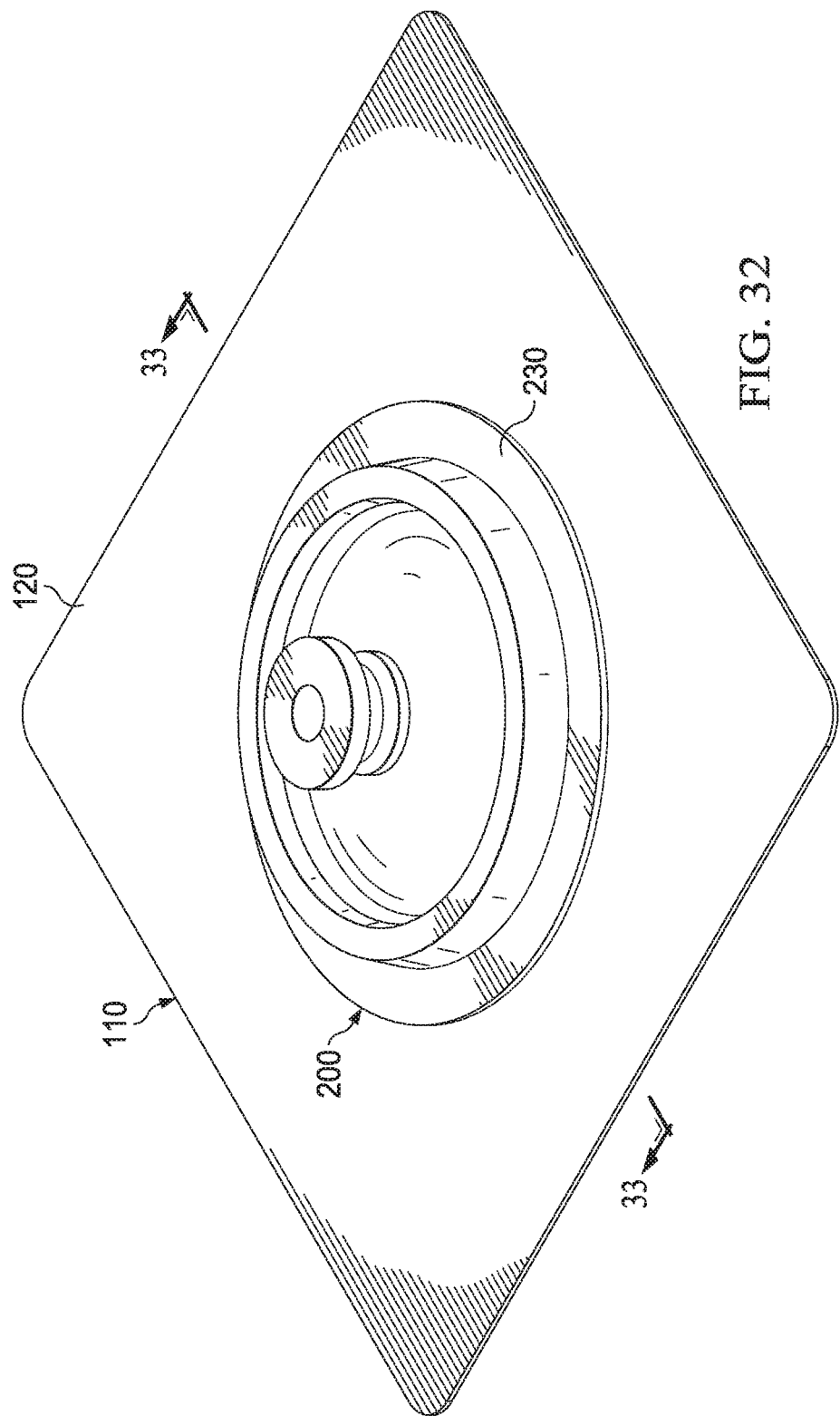
FIG. 32 is an isometric view of an example of a dressing that may be associated with some embodiments of the therapy system of FIG. 1.

FIG. 32 is an isometric view of an example of the dressing 110 that may be associated with some embodiments of the therapy system 100. As shown in FIG. 32, in some embodiments, the pump 200 may be coupled to the dressing 110. For example, the pump 200 may be coupled to the cover 120. In some embodiments, the pump 200 may be permanently coupled to the cover 120 and may be a single-use pump. If the dressing 110 is removed and discarded, the pump 200 may be discarded along with the dressing 110. In some embodiments, the pump 200 may be releasably coupled with the cover 120. The pump 200 may be coupled to the cover 120 using suitable adhesives. For example, in some embodiments, the base 230 of the pump 200 may be fluidly sealed to the cover 120. In embodiments where the pump 200 is releasably coupled to the cover 120, the pump 200 may be reused. Thus, the pump 200 can be removed from the cover 120 and coupled to a new cover.

Figure 33:
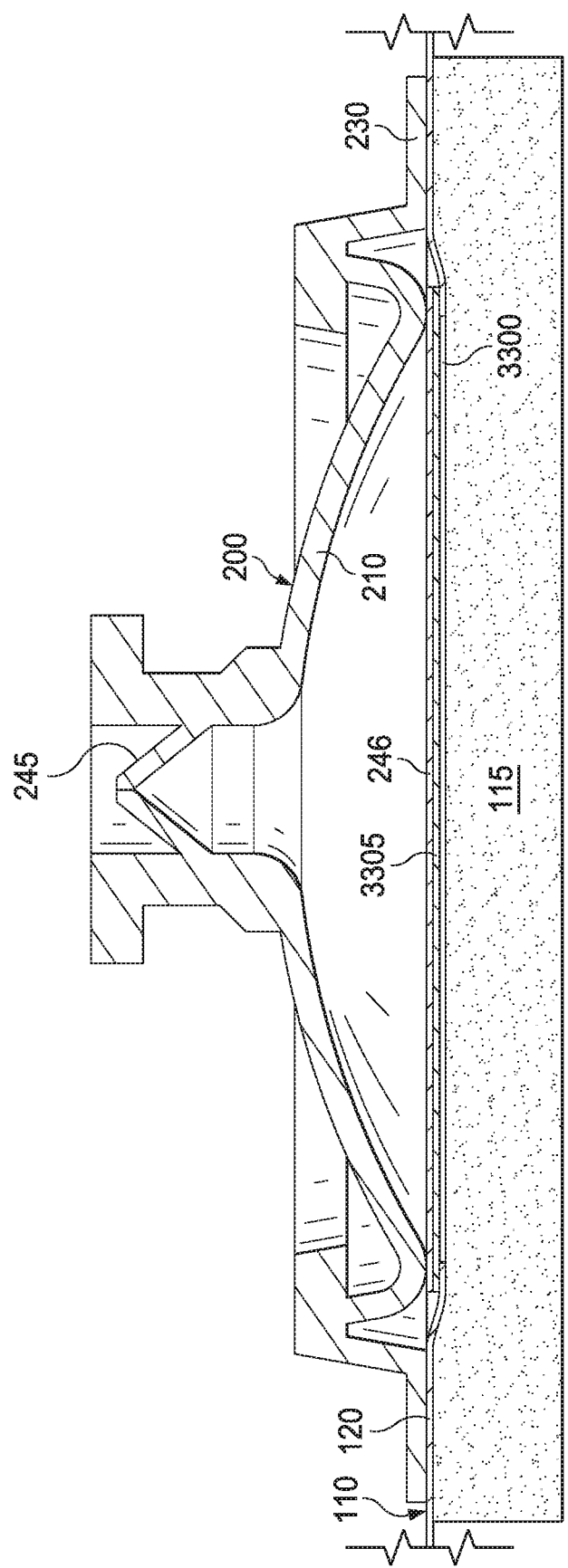
FIG. 33 is a section view of the dressing shown in FIG. 32.

FIG. 33 is a section view of the dressing 110 shown in FIG. 32 along line 33-33. As shown in FIG. 33, the cover 120 may be placed over the tissue interface 115 to create a sealed space between the cover 120 and the tissue site. The pump 200 may be fluidly coupled to the tissue interface 115 through the cover 120. For example, the cover 120 may include an aperture 3300 which provides a fluid path between the tissue interface 115 and the pump 200. The pump 200 may include the chamber assembly 210, the intake valve 246, and the exhaust valve 245. The intake valve 246 of the pump 200 may be fluidly coupled with the tissue interface 115.

As further shown in the example of FIG. 33, in some embodiments a liquid-air separator 3305 may be located between the pump 200 and the cover 120. The liquid-air separator 3305 may serve to prevent the liquid from exiting the tissue interface 115 through the aperture 3300 in the cover 120. The liquid-air separator 3305 may be operably associated with the pump 200 to allow gas communication, but substantially prevents liquid communication between the tissue interface 115 and the pump 200. In an illustrative embodiment, the substantially planar liquid-air separator 3305 may be a hydrophobic or oleophobic filter that prevents passage of liquids into the pump chamber 300. An example of a suitable hydrophobic material includes an expanded PTFE laminate such as a hydrophobic medical membrane manufactured by WL Gore & Associates, Newark, Delaware; the Aspire® ePTFE filter membrane manufactured by General Electric; or any other suitable membrane. In one embodiment, such a laminate may have a 1.0 micron reference pore size on non-woven polyester with a thickness range of about 0.17 millimeters to about 0.34 millimeters. The hydrophobic medical membrane may have a minimum air flow of about 18 LPM/cm$^2$ at 1 bar (15 PSI) and a minimum water entry pressure of 1.1 bar (16.0 PSI). An example of a suitable oleophobic material includes an oleophobic expanded PTFE membrane having a 1.0 micron reference pore size on non-woven polyester with a thickness range of about 0.15 millimeters to about 0.39 millimeters. The oleophobic membrane may have a minimum air flow of about 12 LPM/cm$^2$ at 1 bar (15 PSI) and a minimum water entry pressure of 0.8 bar (12.0 PSI). Alternatively, the substantially planar liquid-air separator 3305 may be a gravity-based barrier system, or a device that includes a hydrophilic surface to encourage condensation or other separation of liquid from a fluid stream when the fluid stream passes over the surface. Other examples of liquid-air separators 3305 may include sintered metals, sintered nylons, specialty fiber filters such as those manufactured by Filtrona, plastics that have been plasma treated to cause the surface to be hydrophilic, or any other material or device that is capable of separating liquid from a fluid stream, or that is otherwise capable of substantially preventing the passage of liquid while allowing the passage of gases.

During operation of the pump 200, on the downward stroke, the pump chamber 300 is compressed, evacuating fluid from the pump chamber 300 through the exhaust valve 245. On the upward stroke, fluid is drawn from the tissue interface 115, through the liquid-air separator 3305, through the intake valve 246, and into the pump chamber 300, expanding the pump chamber 300. This cyclic compression and expansion of the pump chamber 300 creates a negative pressure in the pump chamber 300, wherein this negative pressure may be supplied to the tissue interface 115 to decrease the pressure in the tissue interface 115.

Figure 34:
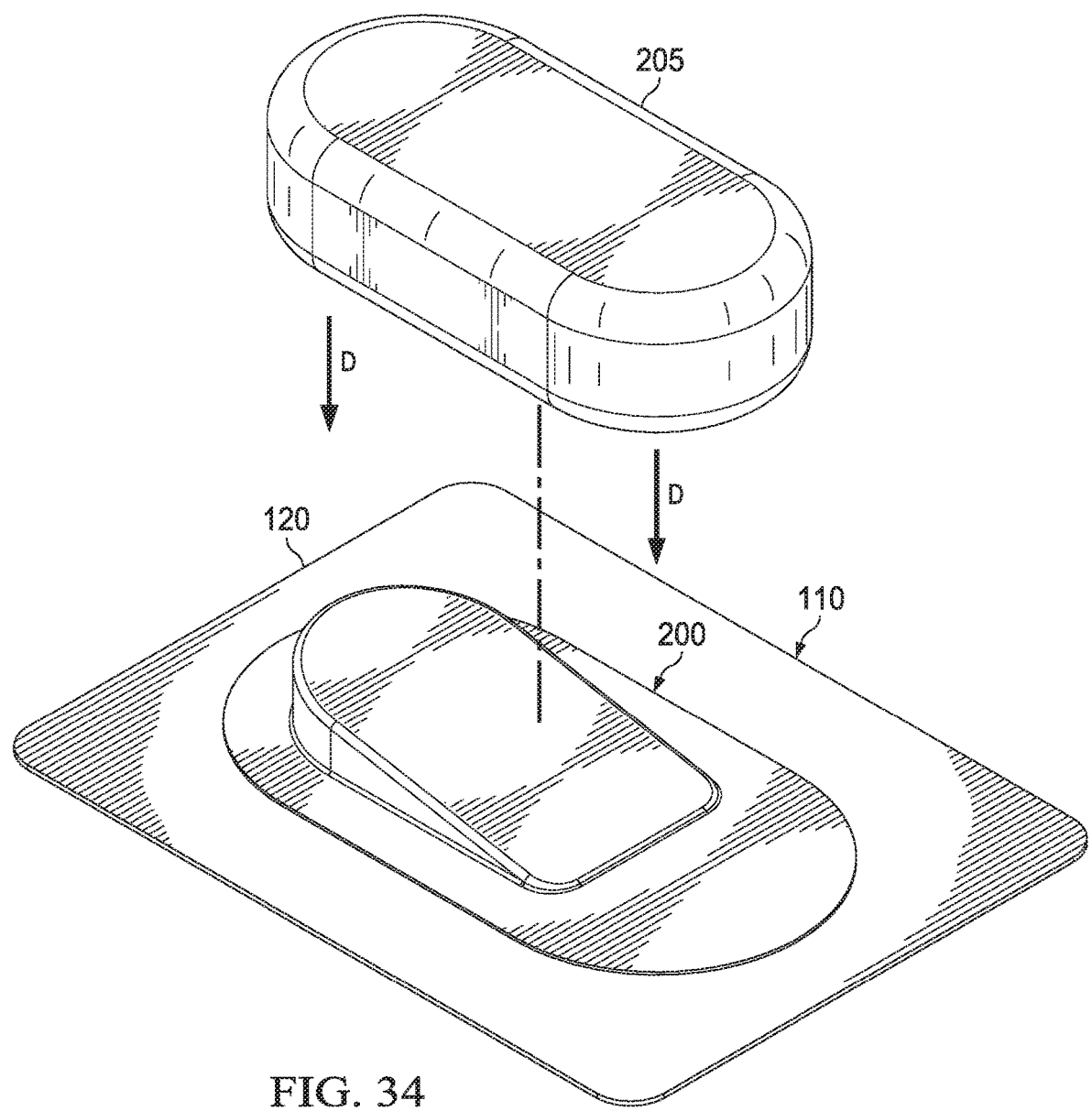
FIG. 34 is an isometric view of another example of a dressing that may be associated with some embodiments of the therapy system of FIG. 1.

FIG. 34 is an isometric view of another example of the dressing 110 that may be associated with some embodiments of the therapy system 100. As shown in FIG. 34, the dressing may include the pump 200, wherein the pump 200 may be a bellows pump. Additionally, the pump actuator 205 may be coupled to the dressing 110 as shown by arrows D.

The systems, apparatuses, and methods described herein may provide significant advantages. For example, the negative-pressure source 105 may be produced in a small size to allow a patient to discretely wear the negative-pressure source 105 under clothing. Additionally, in some embodiments, when the pump 200 is discarded with the dressing 110, the pump actuator 205 may be re-used without needing to replace or sanitize the pump actuator 205. This may particularly be the case where fluid evacuated from the tissue interface 115 does not pass through the pump actuator 205. Additionally, the incidence of fluid leaks between the tissue interface 115 and the negative-pressure source 105 may be reduced due to the coupling of the pump 200 to the dressing 110. This arrangement eliminates additional fluid conductors between the dressing 110 and the negative-pressure source 105.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 125 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site with negative pressure, the dressing comprising:
    a tissue interface adapted to distribute negative pressure across the tissue site;
    a cover adapted to be sealed to epidermis proximate the tissue site; and
    a pump, the pump comprising:
        a chamber wall having a drive surface and a flexible wall extending from the drive surface, the chamber wall defining a pump chamber, the pump chamber fluidly coupled to the tissue interface;
        a base extending from the flexible wall of the chamber wall, the base fluidly sealed to the cover; and
        a cantilever spring disposed within the pump chamber, the cantilever spring coupled to the base;
        a frame coupled to the base, wherein the frame comprises a base portion, the cantilever spring extending from the base portion;
        wherein during operation of the pump, the drive surface is configured to be cycled between an unactuated position and an actuated position, and wherein the drive surface is oriented at a first angle with respect to the base when the drive surface is in the unactuated position; and
        wherein the cantilever spring is configured to return the drive surface to the unactuated position.

2. The dressing of claim 1, wherein the chamber wall is adapted to be compressed to evacuate fluid from the pump chamber.

3. The dressing of claim 2, further comprising an exhaust valve fluidly coupled to the pump chamber and adapted to allow fluid to be evacuated from the pump chamber if the chamber wall is compressed.

4. The dressing of claim 1, wherein the pump chamber is adapted to expand to decrease pressure in the tissue interface.

5. The dressing of claim 1, further comprising an intake valve between the tissue interface and the pump chamber, the intake valve adapted to fluidly couple the pump chamber and the tissue interface and adapted to allow pressure to be reduced in the tissue interface when the pump chamber is expanded.

6. The dressing of claim 5, further comprising a liquid-air separator coupled to the intake valve and adapted to prevent liquid from entering the pump chamber from the tissue interface.

7. The dressing of claim 1, wherein the pump chamber has a teardrop shape or a wedge shape.

8. The dressing of claim 1, wherein the chamber wall comprises a corrugated flexible wall or a concertinaed flexible wall.

9. The dressing of claim 1, wherein the dressing further comprises a wall extending upward from the base, wherein the wall is adapted to orient a pump actuator that is adapted to be secured to the dressing.

10. The dressing of claim 1, wherein the cantilever spring is oriented at a second angle with respect to the base when the drive surface is in the unactuated position, and wherein the first angle and the second angle are equal.

11. The dressing of claim 1, wherein the base portion is located in the base.

12. The dressing of claim 1, wherein:
the base has a first side and a second side, the first side facing the cover, and the chamber wall on the second side; and
the pump further comprises a wall extending from the second side of the base away from the first side of the base, the wall proximate to a perimeter of the base and having an inner side and an outer side, wherein the inner side is perpendicular to the base and the outer side is curved.

13. A dressing for treating a tissue site with negative pressure, the dressing comprising:
a tissue interface adapted to distribute negative pressure across the tissue site;
a cover adapted to be sealed to epidermis proximate the tissue site; and
a pump, the pump comprising:
a chamber wall having a drive surface and a flexible wall extending from the drive surface, the chamber wall defining a pump chamber, the pump chamber fluidly coupled to the tissue interface;
a base extending from the flexible wall of the chamber wall, the base fluidly sealed to the cover;
a frame coupled to the base, wherein the frame comprises a first bridge, the first bridge located a distance away from the base, and the first bridge configured to cooperate with a pump actuator to releasably secure the pump actuator to the dressing; and
a cantilever spring disposed within the pump chamber, the cantilever spring coupled to the base;
wherein during operation of the pump, the drive surface is configured to be cycled between an unactuated position and an actuated position, and wherein the drive surface is oriented at a first angle with respect to the base when the drive surface is in the unactuated position; and
wherein the cantilever spring is configured to return the drive surface to the unactuated position.

14. The dressing of claim 13, wherein:
the base has a first side and a second side, the first side facing the cover and the chamber wall on the second side;
the pump further comprises a wall extending from the second side of the base away from the first side of the base; and
the first bridge located between the chamber wall and the wall.

* * * * *